US005559133A

United States Patent [19]

Girijavallabhan et al.

[11] Patent Number: 5,559,133

[45] Date of Patent: Sep. 24, 1996

[54] ORALLY ACTIVE ANTIVIRAL COMPOUNDS

[75] Inventors: Viyyoor M. Girijavallabhan, Parsippany; Ashit K. Ganguly, Upper Montclair; Richard W. Versace, Wanaque; Anil K. Saksena, Upper Montclair; Patrick A. Pinto, Mine Hill, all of N.J.

[73] Assignee: Schering Corporation, Kenilworth, N.J.

[21] Appl. No.: 167,812

[22] PCT Filed: Jun. 17, 1992

[86] PCT No.: PCT/US92/04961

§ 371 Date: Dec. 16, 1993

§ 102(e) Date: Dec. 16, 1993

[87] PCT Pub. No.: WO92/22520

PCT Pub. Date: Dec. 23, 1992

[51] Int. Cl.[6] .................... C07C 43/225; A61K 31/44; A61K 31/09; C07D 213/63

[52] U.S. Cl. .................... 514/335; 514/277; 514/374; 514/438; 514/461; 514/720; 514/721; 546/261; 546/339; 548/237; 549/78; 549/502; 568/645

[58] Field of Search .................... 568/645; 549/78, 549/502; 546/261, 339; 548/237; 514/720, 721, 461, 438, 374, 335, 277

[56] References Cited

U.S. PATENT DOCUMENTS

| | | | |
|---|---|---|---|
| 4,851,423 | 7/1989 | Girijavallabhan et al. | 514/399 |
| 4,891,449 | 1/1990 | Borden et al. | 568/645 |
| 5,041,604 | 8/1991 | Saito et al. | 568/645 |
| 5,350,772 | 9/1994 | Girijavallabhan et al. | 568/645 |

FOREIGN PATENT DOCUMENTS

| | | | |
|---|---|---|---|
| 5639886 | 10/1980 | Australia | 546/149 |
| 0028305 | 5/1981 | European Pat. Off. . | |
| 0099933 | 2/1984 | European Pat. Off. . | |
| 0274867 | 7/1988 | European Pat. Off. . | |
| 0407217 | 1/1991 | European Pat. Off. . | |
| 2418571 | 11/1974 | Germany . | |
| 50-09785 | 4/1975 | Japan . | |
| 9100858 | 1/1991 | WIPO | 548/342 |

OTHER PUBLICATIONS

Rasshofer, W. et al. Chemische Berichte 1978 vol. III pp. 1108–1125.

CA 83 163816Y, Morikawa, et al. (Japanese 75 09785).

Morikawa, H. et al. Chem Abstracts 1975 vol. 83 Abst #163817z.

Karrer, F. et al. Chem. Absracts 1975 vol. 82 (No. 13) Abst #86207a.

Geratz, J. D. et al. J. Medicinal Chem (1976) vol. 19(#5) 634–639.

Tidwell, R. R. et al. Thrombosis Research (1980) vol. 19 339–349.

Chauhan, P. M. S. et al. Indian Journal of Chemistry (1908) vol. 27B pp. 38–42.

*Primary Examiner*—Joseph E. Evans
*Attorney, Agent, or Firm*—Thomas D. Hoffman

[57] ABSTRACT

A compound represented by formula I, $Ar_1$—O—M—O—$Ar_2$, wherein $Ar_1$ and $Ar_2$ are independently substituted phenyl or substituted pyridinyl, the substituents on said phenyl or pyridinyl being independently selected from one, two or three of ($C_1$–$C_{10}$) alkyl, ($C_1$–$C_{10}$) alkoxy, halogen, carbamyl, ($C_1$–$C_{10}$) alkoxycarbonyl, oxazoyl, and ($C_1$–$C_{10}$) alkyl substituted by halogen, ($C_1$–$C_{10}$) alkoxy, hydroxy, or ($C_1$–$C_{10}$) alkoxycarbonyl;

M is

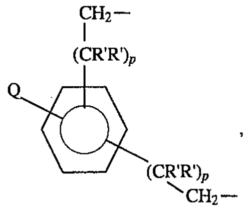

M-1

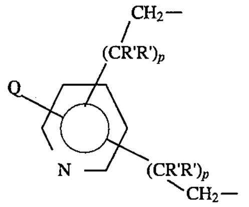

M-2

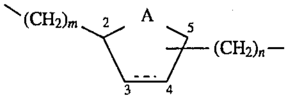

M-3

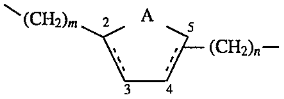

M-4

O is oxygen; R' is ($C_1$–$C_3$ alkyl or H; A is oxygen or sulfur; Q is selected from hydrogen, halogen, nitro, ($C_1$–$C_6$) alkyl, ($C_1C_6$) perhaloalkyl, ($C_1$–$C_6$) alkylthio ($C_1$–$C_6$) or alkyl sulfonyl; the dotted lines in M-3 and M-4 between carbons, 2 and 3 and 3 and 4, and 4 and 5 mean that the bonds between carbons 2 and 3, and 3 and 4, and 5 and 6, may each be a single or double bond; n=1 or 2; m=1 or 2; p=0 or 1; or pharmaceutically acceptable salts thereof as well as pharmaceutical compositions containing such compounds and methods of treating or preventing viral infections, especially picornaviral infections using the compounds of formula I, are disclosed.

13 Claims, No Drawings

ORALLY ACTIVE ANTIVIRAL COMPOUNDS

This application is a 371 of PCT/0592/04-861 filed 06/17/1992.

BACKGROUND

This invention relates to compounds having antiviral activity, pharmaceutical composition containing these antiviral compounds and use of these compounds lot the preparation of a medicament for treating and/or preventing vital infections and methods of treating and/or preventing vital infections, especially picomaviral infections, in mammals using such pharmaceutical compositions.

U.S. Pat. No. 4,851,423 and European Patent Applications EP-A 0274867, and EP-A-0407217, generally, disclose compounds, having antiviral, antiinflammatory and platelet activating factor inhibition activities. The pending European Patent Application discloses such compounds which are represented by the following structural formulas I and II

Z—X—Q—Y—W   I

Z—X—Q—Y—W'—Y—Q—X—Z   II pharmaceutically acceptable add addition, basic addition, and quaternary amine salts thereof and pharmaceutically acceptable solvates thereof, wherein each Z is independently tertiary butyl, phenyl, naphthly or adamantanyl; substituted phenyl, wherein the substituents are one or more of halogen, lower alkoxy, phenoxy, nitrile, nitro, phenylsulfonyl, loweralkylsulfonyl, oxazol-2-yl, lower alkanoyl, benzoyl, lower alkoxycarbonyl, lower alkyl, phenyl, lower alkylthio, phenylaminothiocarbonyl, or lower alkylaminothiocarbonyl; 4 to 6 membered unsubstituted or substituted heterocyclic ring containing at least one nitrogen in the ring with the remaining members of the ring being at least one carbon, and optionally sulfur or oxygen wherein the substituents are one or more or—COOH, —$CH_2OH$, lower alkyl, lower alkylcarbonyl, or aryl lower alkyl;

X and Y are each independently a bond, —O—, —S—, —$SO_2$—,

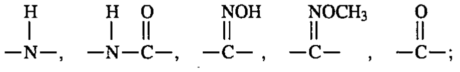

each Q is independently a divalent substituted or unsubstituted, straight or branched chain lower alkanediyl, loweralkanediyl-cycloalkanediyl-lower alkanediyl, lower alkenediyl, lower alkynediyl, phenylene, dihydrofurandiyl, tetrahydrofurandiyl, tetrahydropyrandiyl, lower alkanediyl-tetrahydrofurandiyl-lower alkanediyl wherein the substituents are one or more of hydroxy, epoxy, fluorine, chlorine, azide, or amino;

W is a monovalent substituted or unsubstituted aryl group or a heterocyclic single or fused ring containing from 4 to 10 ring atoms, at least one hetero atom of which is a nitrogen atom and the remaining ring atoms being at least one carbon and optionally sulfur or oxygen, wherein the substituents are one or more of hydroxy, oxo, amino, carbamoyl, carboxyl nitrile, nitro, lower alkyl, lower alkyoxycarbonyl, halogen, sulfamyl, lower alkoxycarbonyllower alkyl, lower alkythio, lower alkoxy, hydroxy lower alkyl, amino lower alkyl, carboxy lower alkyl, guanidino, thioureido, lower alkyl sulfonylamino, aminocarbonyllower alkyl, allyloxycarbonylmethyl or carbamoyloxylower alkyl, with the proviso that W cannot be substituted or unsubstituted isoxazolyl, W' is divalent W.

However, the compounds of this invention are not specifically disclosed.

European Patent Application EP-A- 0099933 discloses alpha, omega-bis (2-chlorophenoxy)- ($C_1$–$C_6$) alkylene-4, 4'-dicarboxylic acid and its lower alkyl esters which are useful as starting materials for producing polyester fibers or films.

Chem. Ber. 111 (1978) 1108–1125 discloses noncyclic crown ethers with central pyridine units substituted at the 2 and 6 positions with 2 -and 2, 6-substituted phenyloxy methylene donor groups; these crown ethers form stoichiometric crystalline complexes with alkaline and alkaline earth and heavy metal ions.

Chemical Abstracts, Vol. 83 (1975) 163817z discloses p-xylene diphenylether derivatives having fungicidal and herbicidal activities.

European Patent Application EP-A-0028305 discloses substituted diaryl mono-loxy- (but not bisaryloxy) compounds which are active against viruses, especially rhinoviruses.

None of these references disclose the compounds of this invention.

SUMMARY OF THE INVENTION

The present invention provides a compound represented by formula I $Ar_1$—O—M—O—$Ar_2$   I wherein $Ar_1$ and $Ar_2$ are independently substituted phenyl or substituted pyridinyl, the substituents on said phenyl or pyridinyl being independently selected from one, two or three of ($C_1$–$C_{10}$) alkyl, ($C_1$–$C_{10}$) perhaloalkyl, ($C_1$–$C_{10}$) alkoxy, halogen, carbamyl, di ($C_1$–$C_{10}$) alkylcarbamoyl ($C_1$–$C_{10}$) alkoxycarbonyl, oxazolinyl, and ($C_1$–$C_{10}$) alkyl substituted by ($C_1$–$C_{10}$)alkoxy, hydroxy, or ($C_1$–$C_{10}$) alkoxycarbonyl;

M is

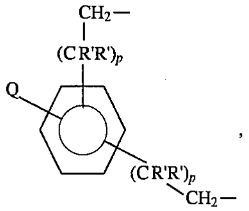

M-1

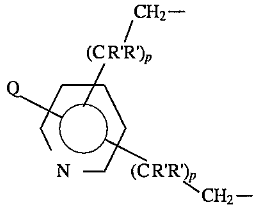

M-2

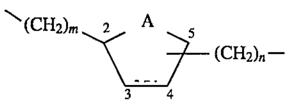

M-3

-continued

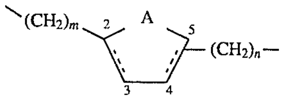

M-4

$(C_4-C_8)$ alkylene, $(C_4-C_8)$ alkenylene or $(C_4-C_8)$-alkynylene;

O is oxygen;

R' is $(C_1-C_3)$ alkyl or H;

A is oxygen or sulfur;

Q is selected from hydrogen, halogen, nitro, $(C_1-C_6)$alkyl, $(C_1-C_6)$perhaloalkyl, $(C_1-C_6)$alkylthio and $(C_1-C_6)$alkylsulfonyl;

the dotted lines in M-3 and M-4 between the carbons 2 and 3, 3 and 4, and 4 and 5 mean that the bonds between carbons 2 and 3, 3 and 4 and 4 and 5 may be each a single or double bond;

n=1or 2 m=1or 2 p=0 or 1 and or pharmaceutically acceptable salts thereof.

The present invention, in a preferred embodiment, provides a compound represented by formula II or III $Ar_{1a}—O—M—O—Ar_{1b}$ II $Ar_{2a}—O—M—O—Ar_{2b}$ III wherein $Ar_{1a}$ and $Ar_{1b}$ are independently selected from phenyl substituted by one, two or three of $(C_1-C_6)$ alkyl, $(C_1-C_6)$ perhaloakyl, $(C_1-C_6)$ alkoxy, halogen, oxazolinyl, carbamyl, di $(C_1-C_6)$ alkylcarbamoyl $(C_1-C_6)$ alkyl substituted by $(C_1-C_6)$ alkoxy, hydroxy or $(C_1-C_6)$ alkoxycarbonyl:

$Ar_{2a}$ and $A_{2b}$ are pyridinyl substituted by one, two or three of $(C_1-C_6)$ alkyl, $(C_1-C_6)$ perhaloalkyl, $(C_1-C_6)$ alkoxy, halogen, oxazolinyl, carbamyl, di $(C_1-C_6)$ alkylcarbamyl, $(C_1-C_6)$- alkyl substituted by $(C_1-C_6)$ alkoxy, hydroxy or $(C_1-C_6)$ alkoxycarbonyl;

M is 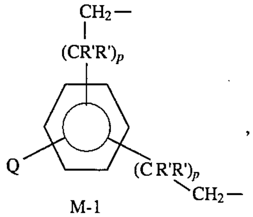 ,

M-1

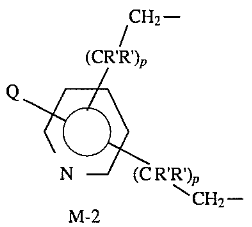

M-2

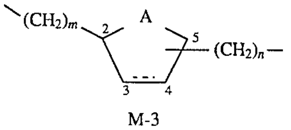

M-3

-continued

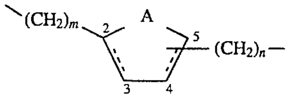

M-4

$(C_4-C_8)$ alkenylene or $(C_4-C_8)$ alkynylene;

O is oxygen;

R' is $(C_1-C_3)$ alkyl or H;

A is oxygen or sulfur;

Q is selected from hydrogen, halogen, nitro, $(C_1-C_6)$ alkyl, $(C_1-C_6)$perhaloalkyl, $(C_1-C_6)$alkylthio and $(C_1-C_6)$ alkylsulfonyl;

the dotted lines in M-3 and M-4 between the carbons 2 and 3, 3 and 4, and 4 and 5 mean that the bonds between carbons 2 and 3, 3 and 4 and 4 and 5 may be each a single or double bond;

n=1or 2 m=1 or 2 p=0 or 1 and or a pharmaceutically acceptable salt thereof

The present invention also provides a pharmaceutical composition for treating viral infections which comprises an antivirally effective amount of a compound of formula I, II, or III and a pharmaceutically acceptable carder. Pharmaceutical compositions adapted for oral administration of a compound of this invention are preferred. adapted for oral administration of a compound of this invention are preferred.

The present invention further provides a use of a compound of formula I, II, or III for the preparation of a medicament treating a viral infection in a mammal afflicted with a viral infection.

The present invention further provides a method for treating and/or preventing a picomaviral infection in a mammal in need of such treating or preventing which comprises administering to said mammal an antipicornavirally effective amount of a compound of formula I, II, or III or a pharmaceutical composition containing said compound.

DETAILED DESCRIPTION OF THE INVENTION AND OF THE PREFERRED EMBODIMENTS

We have found that, the compounds of this invention, compared to the prior art compounds, have superior antiviral activity, exhibit oral activity and a broader spectrum of antiviral activity.

Some of the compounds of this invention may exist in isomeric forms due to the presence of a double bond or one or more chiral centers. All such isomers both in pure form and in admixture, including racemic mixtures are considered to be part of this invention.

The compounds of this invention have been found to be active against ether-resistant RNA viruses, i.e. picomaviruses which includes enteroviruses and rhinoviruses. The enteroviruses include poliovirus, coxsackieviruses and echoviruses. Rhinoviruses include those viruses associated with the common cold and certain other respiratory ailments. The compounds of this invention have been found to be active against a large numbers of enteroviruses, including poliovirus-2, coxsackieviruses A9, A21 and B1, and Echo 4, 6 and 11. In addition, the compounds of this invention have been found to be active against particular rhinoviruses such as rhinovirus 1A, 1, 14 and 86. The representative compounds of this invention have further been found to exhibit oral activity in the murine poliovirus-encephalitis model. The chemical synthetic steps from commercially or readily available starting materials.

The term "substituted phenyl" means phenyl substituted by one, two or three substituents independently selected from halogen, $(C_1-C_{10})$-alkyl, $(C_1-C_{10})$ perhaloalkyl, $(C_1-C_{10})$ alkoxy, carbamyl, dialkylcarbamyl $(C_1-C_{10})$alkoxycarbonyl, oxazolinyl, and $(C_1-C_{10})$ alkyl substituted by halogen, $(C_1-C_{10})$ alkoxy, hydroxy, or $(C_1-C_{10})$ alkoxycarbonyl.

Preferred substituted phenyl includes phenyl substituted by two substituents selected from $(C_1-C_6)$ alkoxy such as methoxy, and ethoxy and halogen such as Cl and F. More preferred substituted phenyl includes phenyl substituted by two of methoxy, chloro, fluoro or methyl, such as the following:

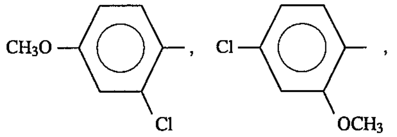
,

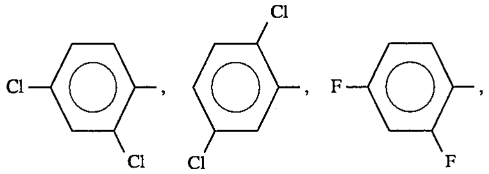
,

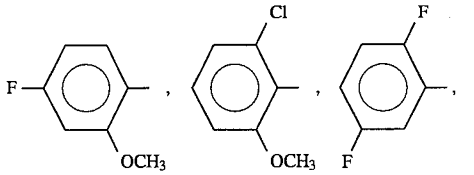
,

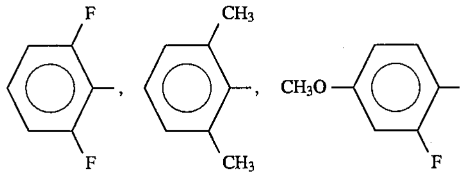
,

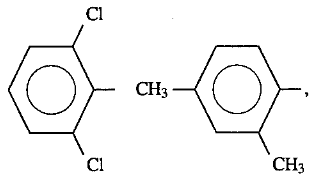
and

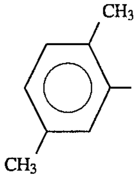

The term "$(C_1-C_{10})$ alkyl" means straight and branched chain alkyl groups of one to ten carbons such as methyl, ethyl, n, and iso-propyl n-iso- sec and tert-butyl, n-, sec, iso, tert- and neo-pentyl, n-, sec-, iso, tert and neo-hexyl and the like.

The term "$(C_1-C_{10})$ alkoxy" means straight and branched chain $(C_1-C_{10})$ alkyl groups univalently-bonded to divalent oxygen.

The term "$(C_1-C_{10})$ perhaloalkyl" means straight and branched chain alkyl groups of one to ten carbon atoms wherein all the hydrogens are replaced by halogen, especially fluorine or chlorine or mixtures thereof. The use of $(C_1-C_6)$ perhaloalkyl is preferred; the use of $(C_1-C_3)$ perhaloalkyl e.g., trifluoromethyl is more preferred.

The term "halogen" includes flouro-, chloro, bromo, and iodo.

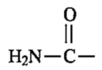

The term "carbamyl" means

The term "di $(C_1-C_{10})$ alkylcarbamoyl" means the two hydrogens in the dialkyl carbamyl are replaced by $2(C_1-C_{10})$ alkyl groups, di$(C_1-C_6)$ alkylcarbamoyl is preferred The term "$(C_1-C_{10})$ alkoxy carbonyl"mean $(C_1-C_{10})$ alkoxy univalently bonded to carbonyl.

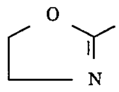

The term "oxazolinyl" means

The term "$(C_1-C_{10})$ alkyl substituted by $(C_1-C_{10})$alkoxy, hydroxy or $(C_1-C_{10})$ alkoxycarbonyl" includes; $(C_1-C_{10})$ alkoxy $(C_1-C_{10})$-alkyl such as methoxymethyl, ethoxymethyl, isoproproxymethyl and the like, hydroxy$(C_1-C_{10})$ alkyl such as hydroxymethyl, and hydroxyethyl; and $(C_1-C_{10})$ alkoxycarbonyl substituted $(C_1-C_{10})$ alkyl such as methoxycarbonylmethyl, ethoxycarbonylethyl, isopropoxycarbonylmethyl and tert-butoxycarbonylmethyl.

The term $(C_4-C_8)$alkylene means $-(CH_2)n-$ wherein n is 4 to 8, preferably n is 6 to 8.

The term $(C_4-C_8)$alkenylene means $-(CH_2)g-(CH{=}CH)_h-(CH_2)_i-$ wherein g and i are independently 1 to 5 and h is 1 or 2 including, for example, cis- and trans- $-CH_2CH{=}CH-CH_2-$, $-CH_2-CH{=}CH-CH_2CH_2-$ or $-CH_2-CH_2-CH{=}CH-CH_2-$, $-CH_2CH{=}CH-CH_2-CH_2\ CH_2-$, $-CH_2-CH_2-CH{=}CH-CH_2-CH_2-$, $-CH_2CH_2-CH_2-CH{=}CH-CH_2-$, $-CH_2-CH{=}CH-(CH_2)_4-$, $-CH_2CH_2CH{=}CH-(CH_2)_3-$, $(CH_2)_3-CH{=}CH-(CH_2)_2-$, $-(CH_2)_4$, $CH{=}CH\ CH_2-$ ,$-CH_2-CH{=}CH-(CH_2)_5-$, $-CH^2-CH_2-CH{=}CH(CH_2)_4-$, $(CH_2)_3-CH{=}CH(CH_2)_3-$ or $-(CH_2)_2-CH{=}CH-CH_2-$.

The term $(C_4-C_8)$ alkynylene means $-(CH_2)_r(C{\equiv}C)_s-(CH_2)_t-$wherein t and r are 1 to 5, and s is 1 or 2 including for example $-CH_2-C{\equiv}C-CH_2-$,$-(CH_2)_3-C{\equiv}C-CH_2-$, $-CH_2-C{\equiv}C-CH_2CH_2-C{\equiv}C-CH_2-$, $-(CH_2)_2-C{\equiv}C-(CH_2)_2-$, $-CH_2-C{\equiv}C-(CH_2)_3-$, $-(CH_2)_4-C{\equiv}C-CH_2-$, $-(CH_2)_3-C{\equiv}C-(CH_2)_2-$, $-(CH_2)_2-C{\equiv}C-(CH_2)_3-$, $-CH_2-C{\equiv}C-(CH_2)_4-$, $-(CH_2)_3-C{\equiv}C-CH_2-$, $-(CH_2)_4-C{\equiv}C-(CH_2)_2$, $-(CH_2)_3-C{\equiv}C-(CH_2)_3-$, $-(CH_2)_2-C{\equiv}C-(CH_2)_4-$or $-CH_2-C{\equiv}C-(CH_2)_5-$.

The term "$(C_1-C_3)$ alkyl" means methyl, ethyl n- and isopropyl propyl groups

The term $(C_1-C_{10})$ alkyl, groups means straight and branched chain alkyl groups of one of ten carbons; $(C_1-C_6)$ alkyl groups are preferred.

The term "($C_1$–$C_{10}$) perhaloalkyl" means ($C_1$–$C_{10}$) alkyl groups wherein each hydrogen is replaced by halogen, especially F or Cl; ($C_1$–$C_6$) perhaloalkyl is preferred; perchloromethyl, perfluoromethyl and perfluoroethyl are more preferred.

The term "($C_1$–$C_{10}$) alkylthio" means straight and branched chain alkyl groups of one to ten carbon wherein carbon is univalently bonded to —S—, e.g., $(CH_3)$—$C_2H_5S$—, $CH_3H_{47}S$—and $(CH_3)_2CHS$—. ($C_1$ –$C_6$) alkylthio groups are preferred.

The term "($C_1$–$C_{10}$) alkylsulfonyl" means straight and branched chain alkyl groups of one to ten carbons wherein carbon is univalently bonded to $SO_2$—e.g., $CH_3SO_2$—, $C_2H_5SO_2$—, $C_3H_7SO_2$—and $(CH_3)_2$. ($C_1$–$C_6$) alkylsulfonyl groups are preferred.

In preferred compounds of this invention wherein

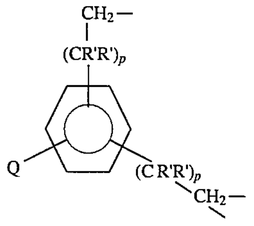

M-1 or

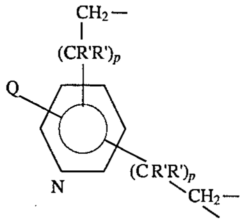

M-2

CR'R' is preferably —$CH_2$—, —$C(CH_3)$—$_2$ or —$CHC_2H$—$_5$ and Q is hydrogen, halogen, especially chlorine or fluorine. Other preferred compounds of this invention include those wherein the dotted lines in M-3 and M-4 represent double bonds, i.e. wherein M is

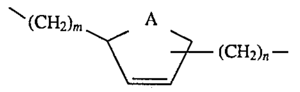

or

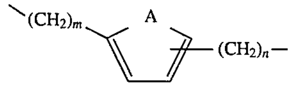

m+n is preferably 2 or 3 and A is O.

The compounds of this invention have been found to be active against ether-resistant RNA viruses, i.e. picornavirused which includes enteroviruses and rhinoviruses. The enteroviruses include poliovirus, coxsackieviruses and echoviruses. Rhinoviruses include those viruses associated with the common cold and certain other respiratoy ailments. Over one hundred serotypes are identified. Although the compounds of this invention are not active against all the rhinoviruses, they are active against a large number of them including the following rhinoviruses 1A, 2, 3, 4, 5 7, 9, 14, 15, 21,36, 39, 41,42, 54, 59, 70, 74, 85 and 86. The compounds of this invention are also active against the enteroviruses such as poliovirus-2, Coxsackieviruses A9, A21 and B1, and Echo 4, 6 and 11.

In addition, the compounds of this invention showed activity when tested in vitro activity assays. The first in vitro antiviral assay performed on the compounds of the invention is plaque reduction assay which measures the ability of compounds to neutralize virus infectivity, e.g. picornavirus infectivity. in tests against poliovirus -2, the $IC_{50}$ values of the compounds of this invention were about 0.008 to about 2.0 microgram/mi. The $IC_{50}$ value in all antiviral tests is the concentration of test compound in micrograms per milliliter "µg/mL" which results in a 50% decrease in plaque forming units compared to a non-treated control.

The second in vitro antiviral assay performed was a modified, premix plaque reduction assay wherein the virus and test compound are mixed and incubated at 37° C. for 1 hr pdor to overlaying with an agar medium. The active compounds of this invention had $IC_{50}$s in this modified premix plaque reduction assay, of from about 0.01 to about 3.0 microgram/mL against poliovirus 2, about 0.05 to about 5 microgram/mL against human rhinovirus 3 and about 0.8 to 5 microgram/mL against cosackievirus A9.

The plaque reduction assay performed as disclosed by Woods, M. G. et al., *Antimicrob Agent Chemother* (1989) Vol. 3, p 2069–2074 involves overlaying HeLa cells with agar medium containing measured concentrations of the test compound following virus absorption, then incubating for 72 hours. The resulting plaques are stained, visualized and measured to determine direct virus growth inhibition as evidenced by plaque reduction with compared to a control.

The modified premix plaque reduction assay measures the capability of a compound to directly inactivate the virus itself and is considered more sensitive because of its ability to discriminate more clearly the virus growth neutralizing effects between compounds whose $IC_{50}$s are close according to the standard plaque reduction assay as disclosed by Woods et al.

The compounds of this invention were tested for antiviral activity in (1) primary in vitro assays with poliovirus -2 by measuring thermal stability, MTT antiviral activity, MTT cytotoxicity therapeutic index and premix plaque reductions (2) MTT-based assays with entroviruses such as Echo 4,6 and 11 and Coxsackieviruses A21, B1 and A9 (3) in HeLa cell viability and (4)in an in vivo murine poliovirus-encephalitis model.

Based on these tests, the preferred antiviral compounds represented by the following structural formulas Ia to Ig were identified:

$Ar_1-O-M-O-Ar_2$

I

| Compound | $Ar_1$ | M | $Ar_2$ |
|---|---|---|---|
| Ia | 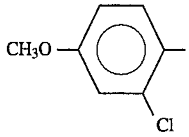 | 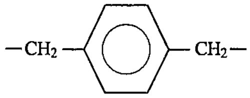 | 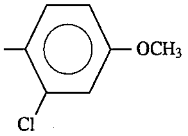 |
| Ib | " | $-(CH_2)_6-$ | " |
| Ic | " | 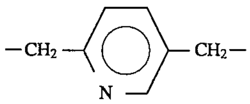 | " |
| Id | " | 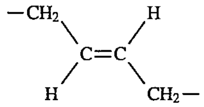 | " |
| Ie | " | $-CH_2C\equiv CCH_2-$ | " |
| If | " | 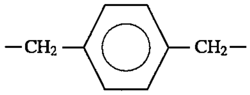 | 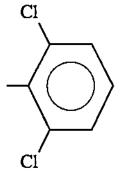 |
| Ig | " | 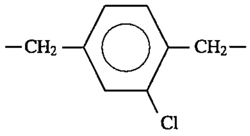 | " |

The compounds of formulas Ia–Ig in the primary screen against (1) (a) poliovirus-2 have $IC_{50}$ thermal stabilities of<10 μg/mL; (b) Therapeutic Indices of (MTT Cytotoxity/ MTT Antiviral) of>50; (c) premix plaque reduction values of<10 μg/mL (2) $IC_{50}$ values of<5.0 μg/mL for 50% of the enteroviruses; (3) $IC_{50}$ values of<50 μg/mL against in the HeLa cell viability model after 24 hrs and (4) showed oral activity in the in-vivo mudne poliovirus-encephaltis model.

The thermal stability test model is a measure of the capability of a compound to interact with the viral capside to alter its characteristics, and thus to inactivate it and to render it incapable of inducing infection. The thermal stability test was run as described by Tisdale, M. et al. in the *J. Antimicrob. Chemother* (1984) Vol. 14, Suppl A, 97–105.

The MTT antiviral and the MTT cytotoxicity assays were based on poliovirus-2 cells propagated and titered in HeLa cells in accordance with the procedure of Mosmann, *T., J. Immunological Methods* (1983), Vol. 65, 55–63.

The MTT antiviral assay measures the capability of a virus to infect and destroy tissue culture cells in vitro.

The MTT cytotoxicity test measures the capability of a chemical synthetic compound to destroy cells, rendering the cells incapable of supporting viral replication in vitro The Therapeutic Index is the ratio of the MTT cytotoxicity to the MTT antiviral activity in HeLa cells based on antiviral assay with a virus, e.g. the poliovirus-2 after 24 hr.

The $IC_{50}$ value for the compounds of this invention is determined by measuring the concentration of the compound which inhibits 50% of virus growth without destroying the tissue culture cells in vitror, endering these cells Incapable of supporting growth.

The oral murine poliovirus-encephalites mode was measured using a solution of the compound in, for example, corn oil or a colloidal suspension of the compound in corn oil in accordance with the procedure of McKinlay, M. A., et al. *Antimicrob Agents Chemother, (*1986) Vol. 29, 30–32.

The compounds of this invention may be administered by any conventional mode of administration by employing and antiviral effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.5 to about 1000 mg/kg of body weight per day may be administered to provide antiviral activity. For example, when administered orally, doses of from about 0.5 to 400 mg/kg of body weight per day, preferably 0.5 to about 200 mg/kg of body weight may be used; and when administered parenterally, e.g., intravenously, dosages of from about 0.1 to about 20 mg/kg body weight may be used.

When administered topically, the amount of compound administered varies widely with the amount of skin being treated, as well as with the concentration of active ingredient applied to the affected area.

The compounds of the present invention may also be administered via oral inhalation or intranasally. Typically the compounds of the invention may be dissolved or dispersed in a pharmaceutically acceptable carrier suitable for use in a nebulizer and/or a metered dose inhaler. Pharmaceutically acceptable carriers include, for example, water, saline, ethanol and the like which form a solution or suspension suitable for administration via oral inhalation in accordance with this invention. If desired, the pharmaceutical composition useful in this invention may also contain minor amounts of non-toxic auxiliary substances such as melting agents, emulsifying agents, preservatives., stabilizers, and pH buffering agents. The preparation of these pharmaceutical compositions is well known to those skilled in the art; see for example Remington's Pharmaceutical Sciences Mack Publishing Co., Easton Pa. 15th Edition (1975).

The compounds of the invention may also be deliverable transdermally for systemic distribution. The transdermal compositions can take the form of creams, lotions and/or emulsions and can be included in transdermal patch of the matrix or reservoir type as are conventional in the art for this purpose.

For the preferred oral administration, the compounds of the invention are typically formulated in the form of tablets, capsules, elixirs, solutions, suspensions and the like preferably solutions. For parenteral administration, they may be formulated into solutions or suspensions. Topical formulations such as lotions, creams, ointments, sprays and mechanical delivery devices, e.g. transdermal can also be made with the compounds of this invention.

Typical pharmaceutically acceptable carriers for use in the formulations described above are exemplified by: sugars such as lactose, starches such as corn starch, cellulose and derivatives such as sodium carboxymethyl cellulose, ethyl cellulose and methyl cellulose vegetable oils, e.g., corn oil, and α-, β- or γ-t-cyclodextrins or the hydroxyalkylated cyclodextrin derivatives as well as other carriers well known in the art. Liquid pharmaceutical compositions can also be preferably α-formulated in solution with an appropriate amount of a hydroxpropyl β-or γ-cyclodextdn having 2 to 11 hydroxpropyl groups per molecule of cyclodextrin, polyethylene glycol, e.g., PEG-200 or propylene glycol, which solutions may also contain water. Pharmaceutical compositions in the form of aqueous solutions suitable for oral use can be prepared by adding a compound of formula I, II or III with a pharmaceutically acceptable carrier such as a hydroxpropylated cyclodextrin in water and adding suitable colorants, flavors, stabilizing, sweetening, solubilizing and thickening agents as desired pharmaceutical compositions in the form of aqueous suspensions suitable for oral use can be made by dispersing the active component in finely divided form in water. A particularly preferred aqueous pharmaceutical composition may be prepared from the compounds of formula I, II or III or together with hydroxypropyl-β-cyclodextrin in water. The use of derivatives of α-, β- and γ-cyclodextrins for example, hydropropyl-β-cyclodextrin are disclosed by N. Bodor U.S. Pat. No. 4,983,586, Pitha U.S. Pat. No. 4,727,064 and Janssen Pharmaceutical International Patent Application No. PCT/EP 5 84/00417.

The pharmaceutical compositions of the present invention may be prepared by admixing the pharmaceutically acceptable carrier e.g., a hydroxypropyl-β-cyclodextrin in water, and adding thereto virally effective amount of a drug of the present invention. The solution so formed is filtered, and optionally, the water may be removed by well known methods, e.g., rotatory evaporation or lyophilization. The formation of the solution may take place at a temperature of about 15° to 35° C. The water is normally sterilized water and may also contain pharmaceutically acceptable salts and buffers, e.g., phosphate or citrate as well as preservatives. The molar ratio of the antiviral compound of formula I to hydroxpropyl-β-cyclodextrin is about 1:1 to 1:80, preferably 1:1 to 1:2. Normally the hydroxypropyl-β-cyclodextrin is present in molar excess. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, e.g. the age and weight of the individual being treated, the mode of administration, the potency of the administered compound, the indication for which the drug is administered and the severity of the ailment being treated.

Typically, the preferred dosage administered per day for treating viral infections will be oral administration of from about 0.5 mg/kg to about 200 mg/kg daily in single or divided doses, with about 0.1 mg/kg to about 60 mg/kg being more preferred.

The compounds of this invention represented by formula I, II or III are prepared by reaction Schemes A, B and C using commercially available starting materials and simple chemical reactions.

Scheme A

1. HO—M—OH ⟶ LG—M—LG
   11 12

2. $Ar_1OH$ + LG—M—LG $\xrightarrow{NaOH}$ $Ar_1O$—M—LG
   10 12 14

3. $Ar_2OH$ + 14 $\xrightarrow{NaOH}$ $Ar_1O$—M—O—$Ar_2$
   16 I

Compound 11 is reacted with for example, mesyl chloride in the presence of base e.g. triethylamine (TEA) in an aprotic solvent e.g., $CH_2Cl_2$ at 0° to 20° C. to produce compound 12; reaction of the mesylate with Na[provides the diiodide compound 12.

Phenol 10, e.g. 2-chloro-4-methoxyphenol is reacted with compound 12 wherein LG is a leaving group such as Br, I, mesylate or tosylate in the presence of an alkali metal hydroxide such as NaOH. The reaction No. 2 takes place at a temperature of about −20° C. to 60° C. in an inert, organic solvent such as dimethylsulfoxide (DMSO), dimethyl formamide (DMF) or tetrahydrofuran (THF). Compounds of formula 14 are isolated by addition of water and the crude product is purified by crystallization and/or column chromatography. Compound 14 is reacted with phenol 16 under reaction conditions similar to those employed in reaction No. 2 to produce compound of formula I, II, or III Scheme A or B is employed wherein compounds 10 and 16 are different.

Scheme B

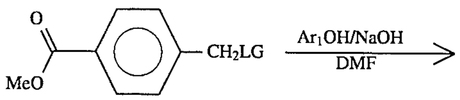

20

-continued

Scheme B

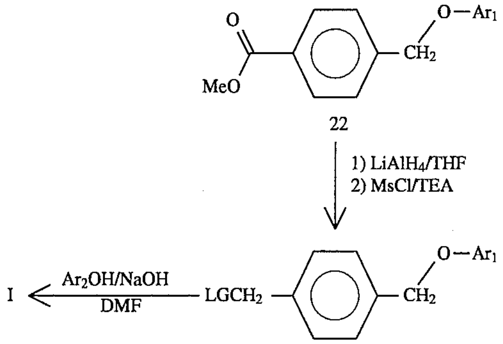

22

24

LG = MSO, Cl or I

Scheme B is particularly preferred for preparation of compounds of formula I, II, or III wherein M is

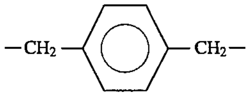

and $Ar_1$ and $Ar_2$ are different. Compounds 20 wherein LG are Br is commercially available. Compound 20 wherein LG is mesylate or chloro is prepared by reaction of commercially available methyl 4(hydroxymethyl)benzoate with mesyl chloride. Reaction of 20 with $Ar_1OH$ is preformed as described in Scheme A to form Compound 22. Reduction of 22 by a metal hydride e.g. $LiAlH_4$ in an aprotic ether, e.g., THF gives the benzyl alcohol 23 (not shown) which is converted into the mesylate 24 by standard procedures. Reaction of 24 with the sodium salt of phenol $Ar_2OH$ in e.g. DMF provides compounds of formula I, II, or III.

In the cases wherein compounds 10 and 16 are identical, Scheme C is used.

Scheme C

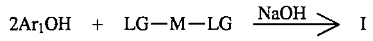

12

Scheme

The preparation of the compounds of formula I, II, or III is also exemplified by the following synthetic sequences using standard chemical reactions and known or commercially available starting materials well known to the synthetic organic chemist.

1. 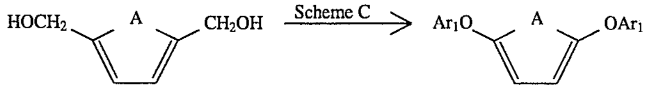

A = S or O

2. 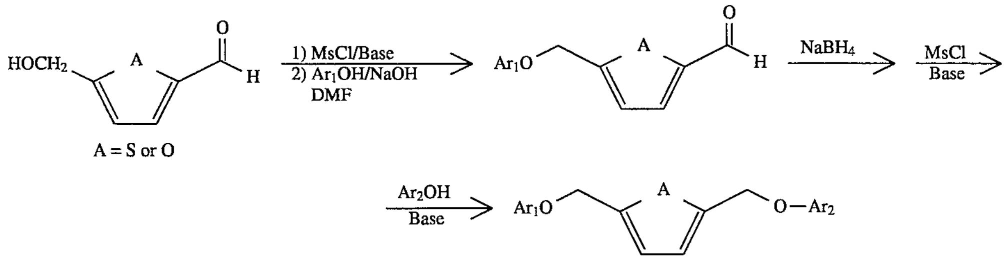

A = S or O

3. 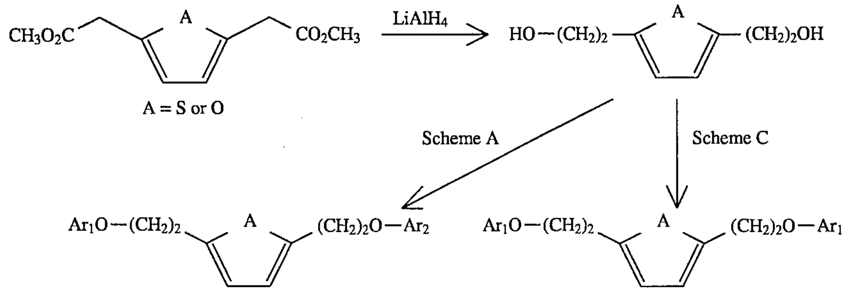

A = S or O

4. 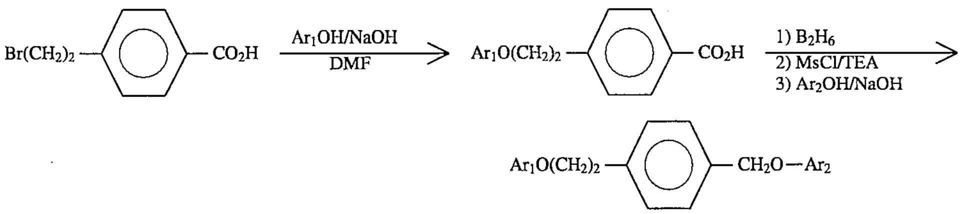

-continued
5.
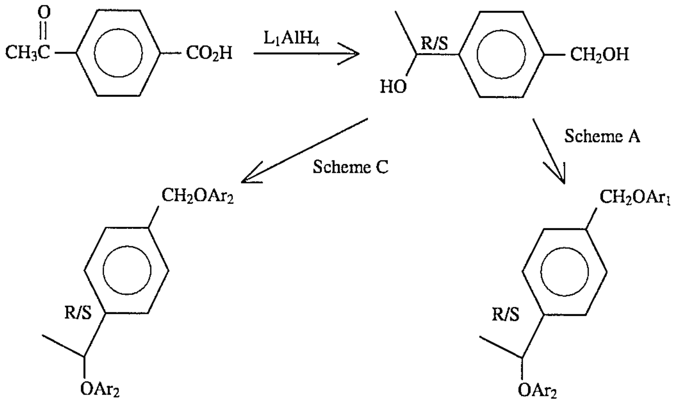
6.
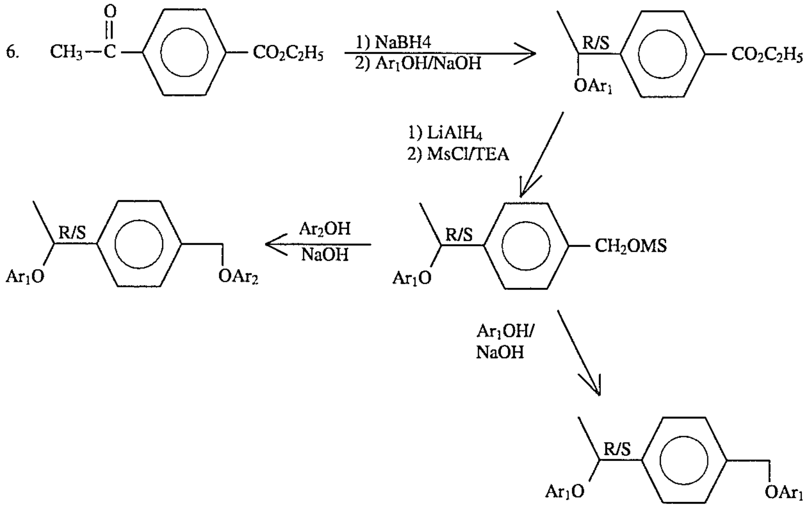
7.
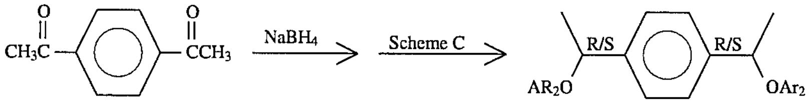
8.
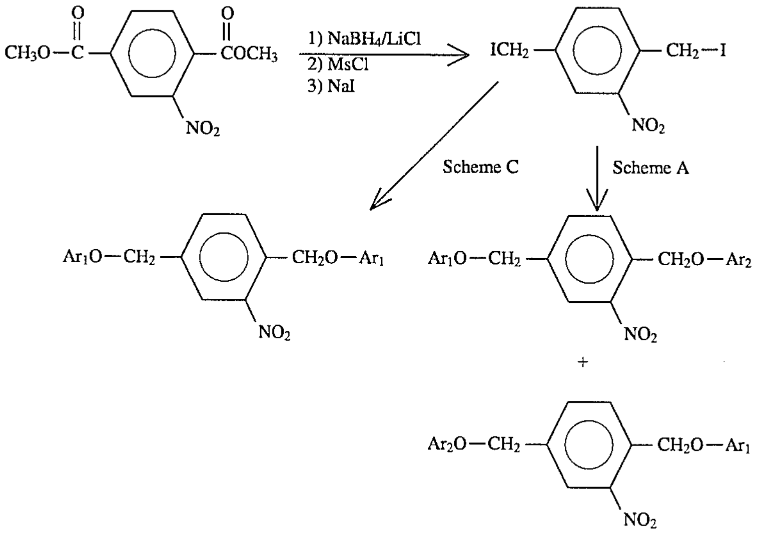

-continued
9.
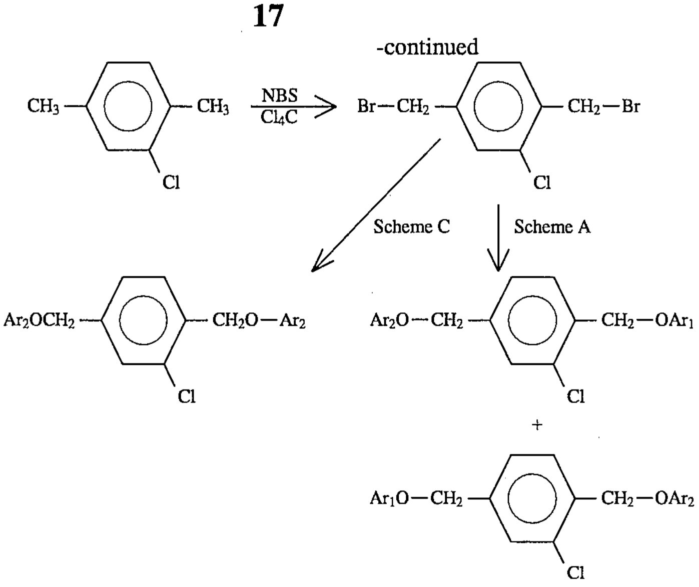
10.
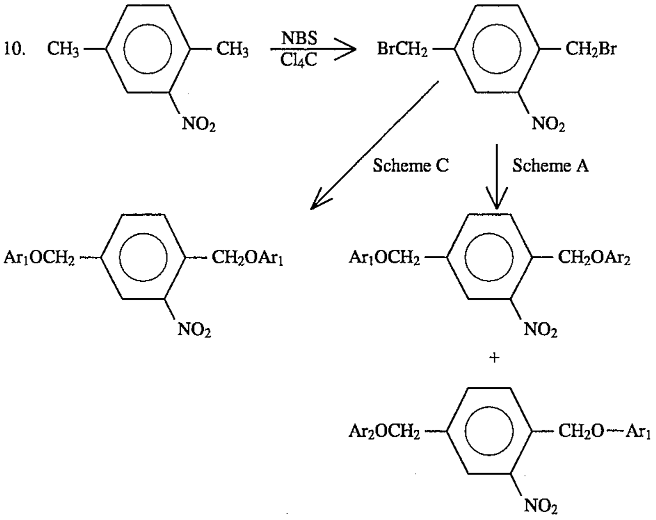
11.
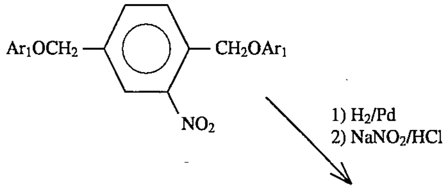

-continued

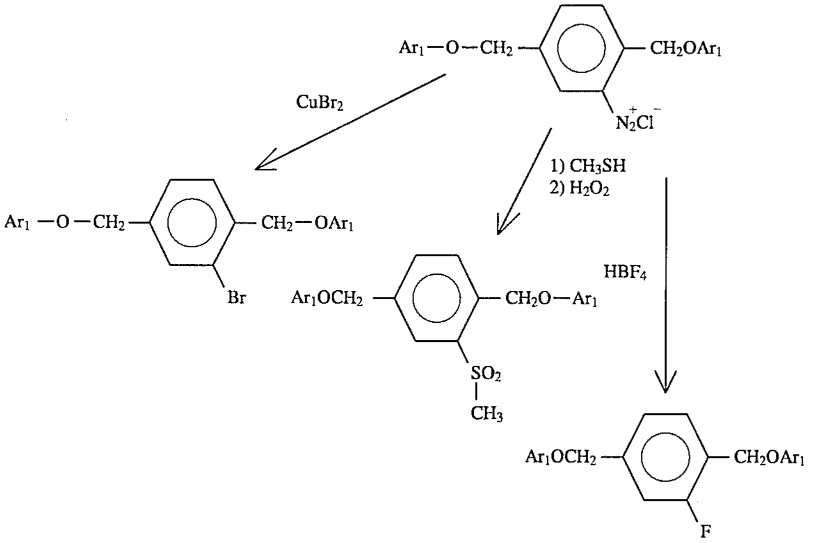

The reductions in reactions D-2, 3, 4, 5, 6, 7 and 8 are described by H. O. House, *Modern Synthetic Reactions*, 2nd Edition W. A. Benjamin Inc. 1972. The Sandmeyer reactions in D-11 are described by March in *Advanced Organic Chemistry: Reactions, Mechanisms and Structure* McGraw-Hill, New York 1968, p 553 to 554.

The separation of the products of reactions 8, 9, 10 and 11 in Scheme D may be accomplished by standard chromatographic techniques such as thin layer, column or high performance liquid chromatography.

The separation of the compounds HO—M—OH having chiral centers such as produced by reactions 5, 6, and 7 in Scheme D may be resolved into the separate enantiomers having the R or S absolute configuration by use of standard resolution techniques.

For reviews of resolution methods, see S. H. Wilen, Top. Sterochem. 6, 107 (1971); S. H. Wilen, A. Collet, and J. Jacques, Tetrahedron 33, 2725 (1977); A. Collet, M. J. Brienne, and J. Jacques, Chem. Rev. 80, 215 (1980); J. Jacques, A. Collet, and S. H. Wilen, Enantiomers Racemates and Resolutions, Wiley-Interscience, New York, 1981.

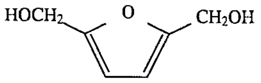

(A=O)

or reaction 3, e.g.

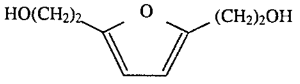

(A=O)

may be hydrogenated (e.g., $H_2$/Pd) to the saturated molecules and those molecules Which are optically active may be resolved as described hereinabove.

The structural formulas of the compounds of the Examples were determined by analysis of PNMR and mass spectra.

EXAMPLES 1–5

TABLE I

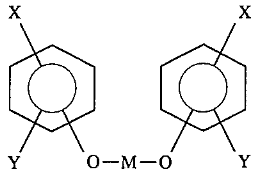

IV

| Example | X | Y | M |
|---|---|---|---|
| 1 | 2-Cl | 4-$CH_3O$ | $-(CH_2)_6-$ |
| 2 | " | " | $-(CH_2)_5-$ |
| 3 | " | " | $-(CH_2)_7-$ |
| 4 | " | " | $-CH_2-C\equiv C-CH_2-$ |
| 5 | " | " | 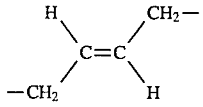 |

Example 1

Add 2 g of 6-(2-chloro-4-methoxyphenoxy)hexyl-1-iodide (prepared in accordance with the procedures of Example 2 (a) of V. M. Girijavallabhan et al in U.S. Pat. No. 4,851,423 issued Jul. 25, 1989 and Diana et al. in J. Med Chem (1985) Vol. 28 p 748–52) to a mixture of 2 g of 2-chloro-4-methoxyphenol and 0.05 g of NaOH in 10 mL of DMF. Stir the so-formed reaction mixture overnight. Partition the reaction mixture with $CH_2Cl_2$ and water. Separate the organic phase and evaporate the solvent to obtain a crude product. Purify the crude product on a silica gel chromatography column by eluting with 100% $CH_2Cl_2$ to provide 1.29 g of 1,1'-[1,6-hexanediyl bis(oxy)]bis-[2-chloro-4-methoxybenzene]

Example 2

Use the procedure of Example 1 except substitute an equivalent amount of 5-[2-chloro-4-methoxyphenoxy]pentyl-1-iodide [prepared in accordance with Example 16(a) of U.S. Pat. No. 4,851,423] for the hexyl-1-iodide of Example 1.

Example 3

Use the procedure of Example 1 except substitute an equivalent amount of 5-[2-chloro-4-methoxyphenoxy)heptyl-1-iodide [prepared in accordance with Example 15(a) of U.S. Pat. No. 4,851,423] for the hexyl-1-iodide of Example 1.

Example 4

Add 1.23 g of 1,4-dichlorobutyne-2 to a mixture of 3.5 g of 2-chloro-4-methoxyphenol and 1.8 g of a 50:50(w/w) mixture of $NaOH:H_{20}$ in 30 mL of DMF. Stir the so-formed mixture overnight at room temperature. Purify the crude product in accordance with the procedure of Example 1 to provide 1,1'-[-1,4-butyne-2-diyl bis(oxy)]bis-[2-chloro-4-methoxybenzene]

Example 5

Add 2.14 g of trans -1,4-dibromobutene-2 to a mixture of 3.5 g of 2-chloro-4-methoxyphenol and 1.8 g of a 50:50 (w/w) mixture of $NaOH:H_2O$ in 30 mL of DMF. Stir the so-formed mixture overnight at room temperature. Purify the crude product in accordance with the procedure of Example 1 to provide 1,1'-[1,4-trans-butene-2-diyl bis(oxy)] bis-[2-chloro-4-methoxybenzene].

Example 6

To a stirred mixture of 10.0 g of 2-chloro-4-methoxyphenol and 2.5 g of NaOH in 50 mL of DMF add 7.0 g of α, α'-dibromo-p-xylene and stir the so-formed reaction mixture at room temperature for 4 hrs. Add 300 mL of water and filter the crude precipitated solid. Purify the crude product by re-crystallization from the methylene chloride to produce 9.12 g of 1,1'-[1,4-phenylene bis(methylenoxy)]-bis [2-chloro-4methoxybenzene] as a pure compound.

Examples 7–14

Follow the procedure of Example 3 except substitute the appropriate substituted phenol for 2-chloro-4-methoxyphenol and the appropriate dibromide for α, α'-dibromo-p-xylene to provide the corresponding product.

TABLE FOR EXAMPLES 6–14

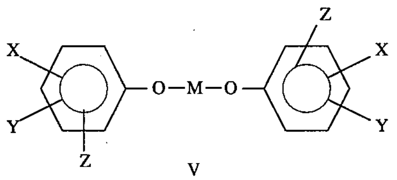

V

| Example No. | X | Y | Z | M |
|---|---|---|---|---|
| 6 | 2-Cl | 4-$CH_3O$ | H | 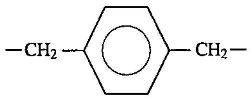 |
| 7 | 2-Cl | 6-Cl | H | 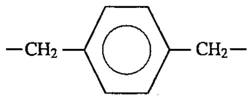 |
| 8 | 2-Cl | 4-$CH_3$ | H | 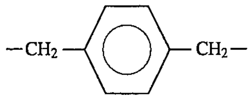 |
| 9 | 2-F | 4-F | H | 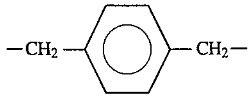 |
| 10 | 2-Cl | 5-$CH_3$ | H | 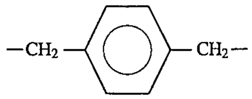 |

-continued
TABLE FOR EXAMPLES 6–14
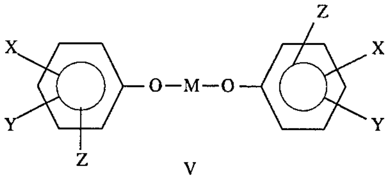
V
| Example No. | X | Y | Z | M |
|---|---|---|---|---|
| 11 | 2-Cl | 4-$CH_3$ | H | 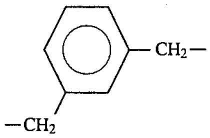 |
| 12 | 2-Cl | 4-$(CH_3)_2CHO$ | H | 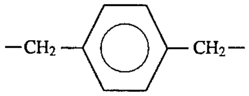 |
| 13 | 2-Cl | 4-$CH_3$— | 5-$CH_3$— | 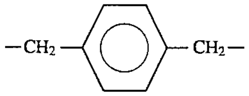 |
| 14 | H | 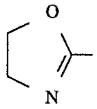 | H | 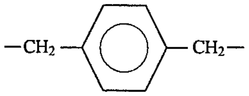 |

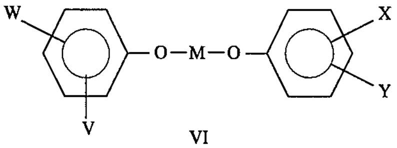
VI
| Example | W | V | M | X | Y |
|---|---|---|---|---|---|
| 15a | 4-$CH_3O$— | 2-Cl | 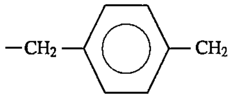 | 2-Cl | 6-Cl |
| 15b | 2-Cl | 4-$CH_3O$— | 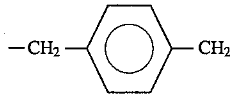 | 2-Cl | 5-Cl |
| 15c | " | " | 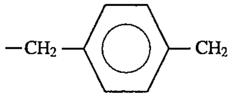 | 2-Cl | 4-Cl |
| 15d | " | " | 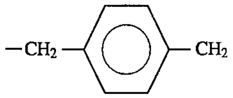 | 2-F | 6-F |
| 15e | " | " | 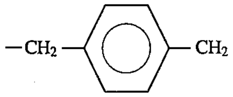 | 2-F | 5-F |
| 15f | " | " | 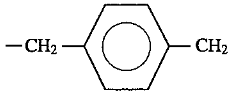 | 2-F | 4-F |
| 15g | " | " | 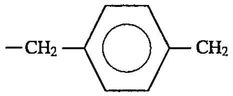 | 2-$CH_3$ | 5-$CH_3$ |
| 15h | " | " | 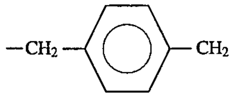 | 2-$CH_3$ | 4-$CH_3$ |
| 15i | " | " | 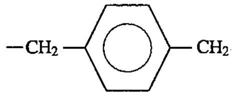 | 2-$CH_3$ | 6-$CH_3$ |
| 15j | " | " | 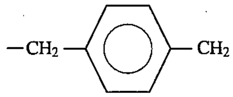 | 2-Cl | 4-$CH_3$ |
| 15k | " | " | 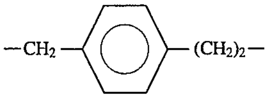 | 2-Cl | 6-Cl |
| 15l | " | " | 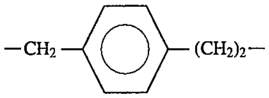 | 2-Cl | 5-Cl |
| 15m | " | " | 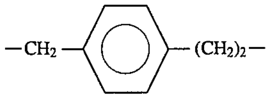 | 2-Cl | 4-Cl |

-continued

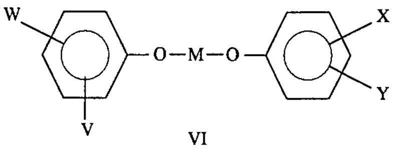

VI

| Example | W | V | M | X | Y |
|---|---|---|---|---|---|
| 15n | " | " | 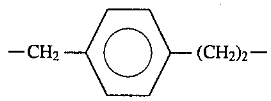 | 2-Cl | 4-$CH_3O$ |
| 15o | " | " | 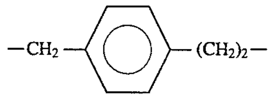 | 2-F | 6-F |
| 15p | 2-Cl | 6-Cl | 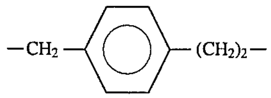 | 2-Cl | 4-$CH_3O$ |
| 15q | 2-Cl | 5-Cl | 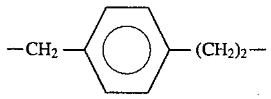 | 2-Cl | 4-$CH_3O$ |
| 15r | 2-Cl | 4-Cl | 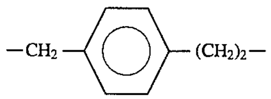 | 2-Cl | 4-$CH_3O$ |
| 15s | 2-F | 6-F | 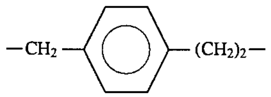 | 2-Cl | 4-$CH_3O$ |
| 15t | 2-F | 5-F | 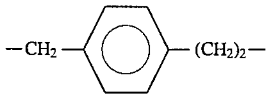 | 2-Cl | 4-$CH_3O$ |
| 15u | 2-F | 4-F | 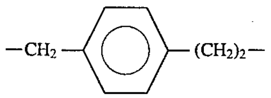 | 2-Cl | 4-$CH_3O$ |
| 15v | 2-$CH_3$ | 6-$CH_3$ | 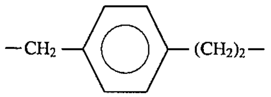 | 2-Cl | 4-$CH_3O$ |
| 15w | 2-$CH_3$ | 5-$CH_3$— | 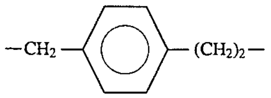 | 2-Cl | 4-$CH_3O$ |
| 15x | 2-$CH_3$ | 4-$CH_3$ | 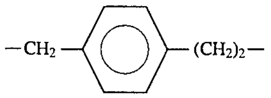 | 2-Cl | 4-$CH_3O$ |

Example 15a

A. Add 5 g of 2-chloro-4-methoxyphenol to a mixture of 17 g of α,α'-dibromo-p-xylene to a stirred mixture of 2.5 g of 50:50 (w/w) $NaOH:H_{20}$ and 50 mL of DMF. Stir the so-formed mixture for 4 hours. Partition the reaction mixture with methylene chloride and water. Separate the organic layer and remove the solvent by rotary evaporation to obtain a solid residue. Purify the residue on a silica gel chromatography column using pure hexane to pure methylene chloride as the eluants to provide 8 g of 1-[4-bromomethylbenzyloxy]-2-chloro-4methoxyphenyl ether.

B. To a solution of 0.50 g of 2,6-dicholorophenol in a mixture of 0.12 g of NaOH in 5 mL of DMF, add 0.50 g of the phenyl ether from Step (A) and stir for 4 hours at room temperature. Add 50 mL of water to the reaction mixture and filter the crude precipitate so-formed. Purify the crude precipitate by crystallization from methylene chloride to provide 350 mg of 2-chloro-1-[[4-[(2,6-dichlorophenoxy)methyl]phenyl]methoxy]-4-methoxybenzene as a pure solid.

Examples 15b–x

Follow the procedure of Example 15(a) except substitute the appropriate phenols and HO—M—OH in steps (A) and (B) of the Example 15a to attain the desired products.

Examples 16–17

TABLE

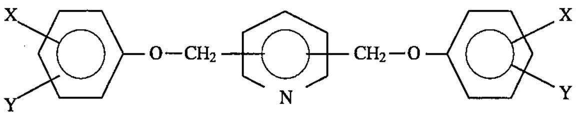

| Example No. | X | Y | 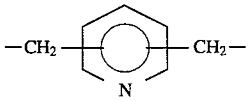 |
|---|---|---|---|
| 16 | 2-Cl— | 4-$CH_3O$— | 2,5-pyridinediylbismethylene |
| 17 | 2-Cl— | 4-$CH_3O$— | 2,6-pyridinediylbismethylene |

Example 16 a) Add 50 mL of thionyl chloride to 25 g of pyridine-2, 5-dicarboxylic acid and heat the so-formed mixture at reflux for 6 hrs. Remove all volatiles by vacuum distillation to obtain crude diacid chloride. Immerse flask containing diacid chloride in an ice-batch and add 100 mL of absolute ethanol thereto. Slowly add 30 mL of triethylamine to the stirred reaction mixture and continue stirring for ½ hr. Add Ethyl acetate/water to stirred reaction mixture and separate the organic layer. Remove the solvent to produce crude product. Recrystallize crude product from hexane/methylene chloride to give 25 g of the pyridine-2,5-bis(ethylcarboxylate).

b) Slowly add 9 g of $NaBH_4$ to a solution of the diester from step (a) in 150 mL of ethanol. Add 13.5 g of $CaCl_2$ as solution in 150 mL of ethanol to the stirred reaction mixture and continue stirring the so-formed reaction mixture overnight. Add 12 g of $H_2SO_4$ and filter off the so-formed solid. Add HCl to adjust to the pH of the solution to about 4. Remove all solvent by rotatory evaporation to produce a crude product. Purify the crude product by crystallization from methanol to produce 11 g of 2,5-bis[hydroxymethyl]-pyridine as the HCl salt.

c) To a solution of 10 g of the pyridine compound of 16b and 32 mL (4 eq) of triethylamine in 250 mL of methylene chloride in a reaction vessel immersed in an ice bath. Add thereto 11 mL (2.5 eq) of $CH_3SO_2Cl$ via a syringe pump. Stir the so-formed reaction mixture for ½ hr after the addition was complete. Partition with methylene chloride and water. Separate the organic layer and remove the solvent to give a crude product which was purified by crystallization from methylene chloride hexane to give 2,5-pyridinediyl bis(methylene mesylate)

d) Follow the procedure of Example 6 except substitute for α, α'-dibromo-p-xylene an equivalent quantity of the bis-mesylate of Example 16 (c) to give 1,1'-[2,5-pyridinediyl bis (methyleneoxy)]bis-[2-chloro-4-methoxybenzene] as a pure solid.

Example 17

Follow the procedure of Example 16 except substitute an equivalent quantity of 2,6-pyridinedicarboxylic acid in step(a) to provide in step (d) 2.1 g of 1,1'-[2,6-pyridinediyl bis(methyleneoxy)]bis-[2-chloro-4-methoxybenzene] as a pure solid.

Examples 18–20

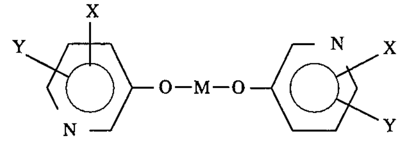

VII

| Example No. | X | Y | M |
|---|---|---|---|
| 18 | 2-Cl | H | 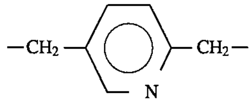 |
| 19 | 4-$CH_3$ | H | " |
| 20 | 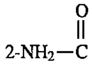 | H | " |

Follow the procedure of Example 6 except substitute an equivalent amount of the appropriate 3-hydroxypyridine for 2-chloro-4-methoxyphenol and substitute an equivalent amount of 2, 5-α, α'-di(bromomethyl)pyridine for α, α'-dibromo-p-xylene to provide the corresponding compound.

Examples 21–23

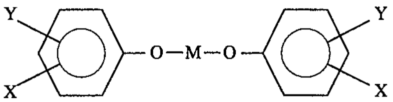

VIII

| Example No. | X | Y | M |
|---|---|---|---|
| 21 | 2-Cl | 4-$CO_2Et$ | 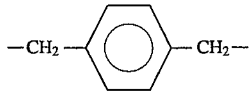 |
| 22 | 2-Cl | 4-$HOCH_2$— | " |
| 23 | 2-Cl | 4-$CH_3OCH_2$— | " |

Example 21

Follow the procedure of Example 6 except add 6 g of α-α'-dibromo p-xylene and substitute 10.0 g of 2-chloro-4 ethoxycarbonyl phenol for 2-Chloro-4-methoxyphenol to obtain 6.8 g of 1,1'-[1,4-phenylene bis(methyleneoxy)]-bis-[2-chloro-4-ethoxycarbonylbenzene].

Example 22

Reduce 5 g of the compound of Example 21 with a solution of 15 of 1 molar $LiALH_4$ in THF at 0° C. Stir the so-formed reaction mixture for 6 hrs. Add thereto 20 mL of a saturated aqueous solution of $NH_4Cl$ and filter off the solids. Remove the solvent from the filtrate to produce a crude product. Purify the crude product by crystallization from $CH_2Cl_2$ to produce 3.6 g of 1,1'[1,4-phenylene bis(methyleneoxy)]-bis-[2-chloro-4-phenylmethanol].

Example 23

To the 1 g of the compound of Example 22 slowly add 5.25 mL of $NaN[(Si(CH_3)_3]_2$. Stir the so-formed reaction mixture for 15 minutes. Add thereto 0.33 mL of $CH_3$ I (neat) and stir the so-formed reaction mixture for 4 hours. Add thereto 200 mL of $H_2O$ and collect the crude product by filtration. Purify the crude product by crystallization from $CH_2Cl_2$ and hexane to produce 750 mg of 1,1'-[1,4-phenylene bis (methyleneo xy)]-bis-[2-chloro-4-( methoxymethyl)benzene]

Examples 24 & 25

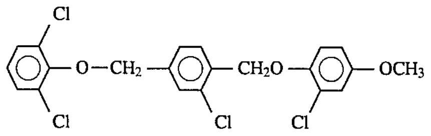

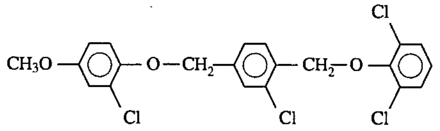

(a) Preparation of 1,4-di(bromomethyl)-2-chlorobenzene

Heat to reflux temperature for 4 hours a solution of 2.8 g of 1,4-dimethyl-2-chlorobenzene; 7.30 g of N-bromosuccimide ("NBS"), 50 mL of $Cl_4C$ and 100 mg of benzoyl peroxide. Remove the solid floating on the reaction mixture surface and remove the $CCl_4$ at reduced pressure to provide a residue. Purify the residue by crystallization from hexane and silica gel column chromatography eluting with hexane to produce 2 g of the title compound as a solid.

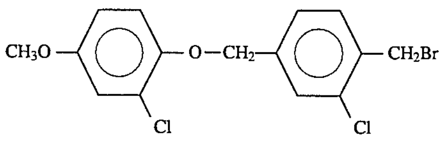

A and

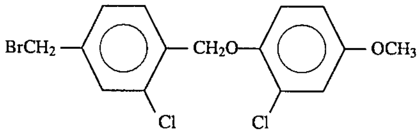

B

To a solution of 7.00 g (18.9 mmoles) of 2-chloro-4-methoxyphenol and 1.58 g (19.8 moles) of NaOH (as a 50% aqueous solution) stirred at room temperature for 10 minutes, add 11.3 g (37.9 mmoles) of the dibromo compound of step (a). Stir the so-formed reaction mixture for 3 hours at room temperature. Place the reaction mixture in a refrigerator overnight. Pour the reaction mixture into 500 mL of $CH_2Cl_2$ and 500 mL of water and stir the so-formed mixture for 5 minutes. Separate and wash the organic layer with brine and dry the separated organic layer over $MgSO_4$. Remove the solvent under reduced pressure to produce a residue. Separate the isomers on silica gel column and combine fractions indicated by TLC to have pure compound. The 200 mHz NMR and mass spectra of the above listed compounds were consistent with the proposed structures.

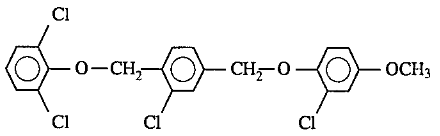

To a solution of 87.1 mg (0.535 mmoles) of 2,6-dichlorophenol and 42.8 mg of NaOH (0.535 mmoles), as a 50% aqueous NaOH solution, in 2 mL of DMF add 100 mg (0.267 mmoles) of the compound A of Step (b). Stir the so-formed reaction mixture at room temperature for 4 hours. Add water, 1N NaOH and ETOAc to the reaction mixture and stir the so-formed mixture for 5 minutes at room temperature. Separate and wash the the organic layer with brine and dry the separated organic layer over $MgSO_4$. Evaporate the organic solvent to produce 133 mg of the title compound. The 200 $MH_z$ NMR and mass spectra were consistent with the proposed structure.

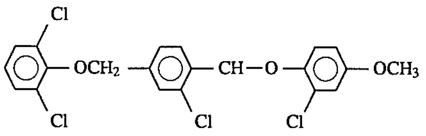

Follow the procedure of step (c) except substitute an equivalent quantity of compound B of step (b) for compound A to produce 130 mg of the compound shown above. The 200 $MH_z$ NMR and mass spectra were consistent with the proposed structure.

Example 26–56

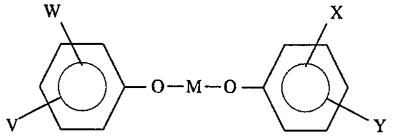

| Example | W | V | M | X | Y |
|---|---|---|---|---|---|
| 26 | 4-$CH_3O$ | 2-Cl | 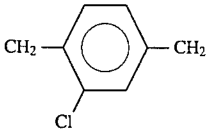 | 2-$CH_3$ | 6-$CH_3$ |
| 27 | " | " | " | 2-$CH_3O$ | 6-Cl |
| 28 | " | " | " | 2-Cl | 5-Cl |
| 29 | " | " | " | 2-Cl | 4-Cl |
| 30 | " | " | " | 2-F | 6-F |

-continued
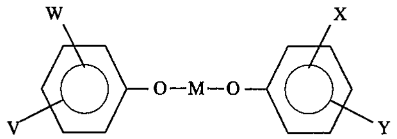
| Example | W | V | M | X | Y |
|---|---|---|---|---|---|
| 31 | " | " | " | 2-Cl | H |
| 32 | " | " | 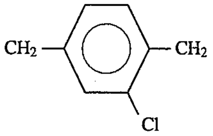 | 2-F | 6-F |
| 33 | " | " | " | 2-Cl | 4-Cl |
| 34 | " | " | " | 2-$CH_3O$ | 6-Cl |
| 35 | " | " | " | 2-$CH_3$ | 6-$CH_3$— |
| 36 | " | " | 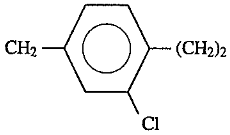 | 2-Cl | 6-$(CH_3)_2CHO$ |
| 37 | " | " | 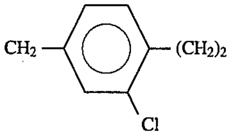 | 2-Cl | 6-Cl |
| 38 | " | " | 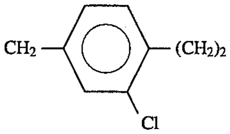 | 2-Cl | 5-Cl |
| 39 | " | " | 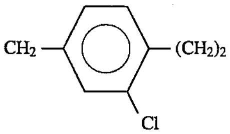 | 2-Cl | 4-Cl |
| 40 | " | " | 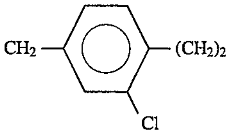 | 2-F | 6-F |
| 41 | " | " | 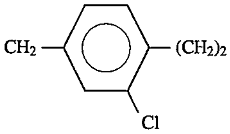 | 2-F | 5-F |
| 42 | " | " | 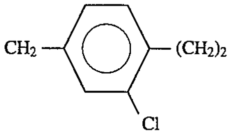 | 2-F | 4-F |
| 43 | " | " | 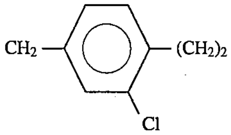 | 2-$CH_3$ | 6-$CH_3$ |

-continued
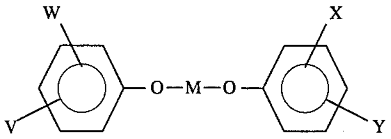
| Example | W | V | M | X | Y |
|---|---|---|---|---|---|
| 44 | " | " | 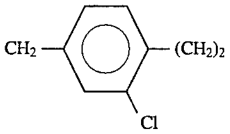 | 2-$CH_3$ | 5-$CH_3$ |
| 45 | " | " | 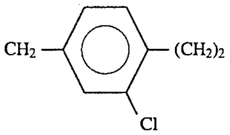 | 2-$CH_3$ | 4-$CH_3$ |
| 46 | " | " | 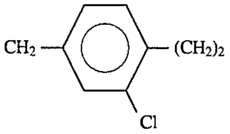 | 2-Cl | 4-$CH_3O$ |
| 47 | 2-Cl | 6-Cl | 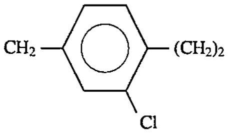 | 2-Cl | 4-$CH_3O$ |
| 48 | 2-Cl | 4-$CH_3O$ | 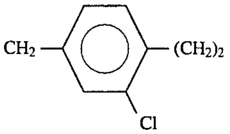 | 2-Cl | 5-Cl |
| 49 | 2-Cl | 4-Cl | 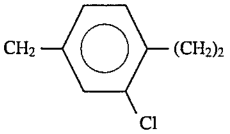 | 2-Cl | 4-$CH_3O$ |
| 50 | 2-Cl | 4-$CH_3O$ | 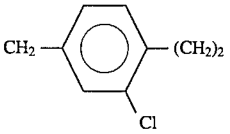 | 2-F | 6-F |
| 51 | 2-F | 5-F | 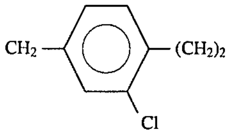 | 2-F | 4-$CH_3O$ |
| 52 | 2-F | 4-F | 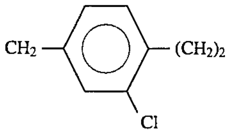 | 2-Cl | 4-$CH_3O$ |
| 53 | 2-$CH_3$ | 6-$CH_3$ | 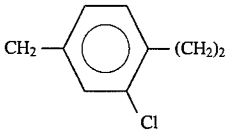 | 2-Cl | 4-$CH_3O$ |

-continued

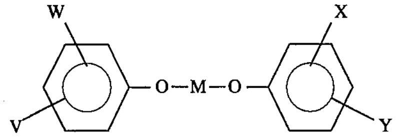

| Example | W | V | M | X | Y |
|---|---|---|---|---|---|
| 54 | 2-$CH_3$ | 5-$CH_3$ | 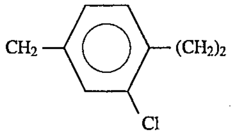 | 2-Cl | 4-$CH_3O$ |
| 55 | 2-$CH_3$ | 4-$CH_3$ | 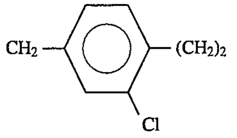 | 2-Cl | 4-$CH_3O$ |
| 56 | 2-F | 6-$CH_3O$ | 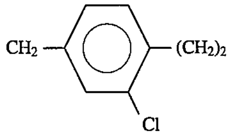 | 2-F | 4-$CH_3O$ |

Follow the procedure of Example 25 except substitute the equivalent amounts of the appropriate phenols $Ar_2OH$ and $Ar_1OH$ and M (as in Scheme A:hereinabove)

Example 57

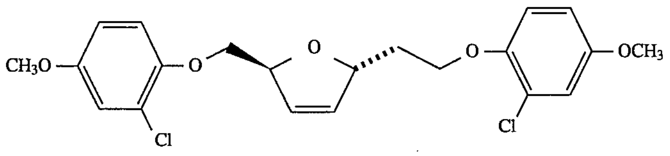

(a) Preparation of

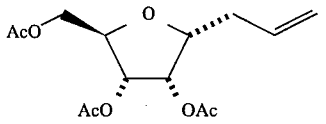

57A (a) Add 35.95 g (0.314 mole, 2 eq) of allyltrimethylsilane and 38.6 ml (0.314 mole, 2 eq) of $BF_3$ etherate to a solution of 50 g (0.15 mole) of β-D-ribofuranose tetracetate in 500 mL of dry $CH_2Cl_2$. Stir the so formed reaction mixture at 25° C. for 2 ½ hours. Add 0.157 moles of allyltrimethylsilane and 0.157 moles of $BF_3$ etherate to the reaction mixture and stir the so formed mixture overnight. No starting material is detected by TLC. Remove solvents under reduced pressure and subject the residue to preparatory column chromatography on silical gel column using ETOAC/Hexane as an eluant to form the allyl triacetate.

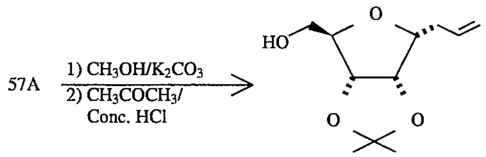

57B (b) Add 68.33 g (0.4945 moles, 3.0 eq) of powdered potassium carbonate to a solution of 49.5 g (0.1648 moles) of the allyltriacetale of step (a)in 500 ml of methanol. Stir the so-formed mixture at 25° C. for 2 hrs. Filter the reaction mixture to remove the excess potassium carbonate and remove the solvents from the filtrate to provide a foamy mass. Dissolve the foamy mass in 20 ml of conc. HCl and 80 mL of acetone over a 10 min period. Dilute the so-formed solution with additive acetone and stir the so-formed mixture for 2 hrs. Add thereto three equivalents of potassium carbonate and stir the so-formed mixture overnight. Remove the excess potassium carbonate by filtration and evaporate the excess acetone, Add thereto $CH_2$ $Cl_2$ and wash the organic layer with water. Purify the crude reaction mixture on silica gel chromatographic column to give 3.5 g of the less polar cis-allyl alcohol acetonide and 28.5 g of the more polar trans-allyl alcohol acetonide.

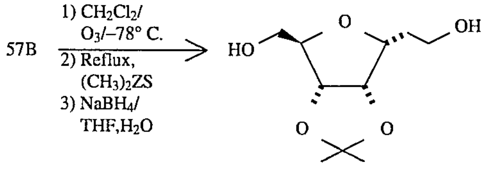

57C (c) To a solution of 1 g (4.67 m mole) of the trans-allyl alcohol acetonide of step (b)in 25 mL of $CH_2Cl_2$ at 78° C. (liquid nitrogen bath) bubble in ozone until the solution is light blue. Quickly purge with $N_2$ gas. Add 5ml of dimethyl sulfide thereto and heat the so-formed reaction mixture at reflux temperature for 3 hours. Remove the solvents at reduced pressure and dissolve the so-formed residue in 10 ml of THF and 3 ml of water. Add thereto 176 mg (4.667 mmoles) of $NaBH_4$. Let stir 2 hrs. Remove the THF at reduced pressure. Add 20 ml of water to the so-formed residue and saturate the water layer with sodium chloride. Extract the aqueous layer with five 10 ml portions of ETOAC. Dry the organic layer over sodium sulfate. Remove the solvent at reduced pressure to give 710 mg of product which crystallizes upon standing overnight. The 200 mHz NMR spectrum is consistent with the proposed structure.

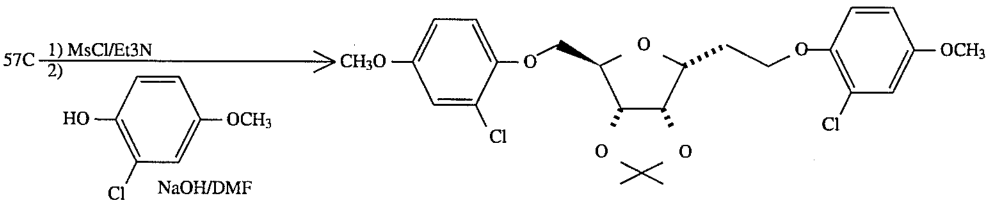

57 D (d) To a solution of 700 mg (3.207 mmoles) of the product of step (c)in 15 ml of dry $CH_2Cl_2$ and 1.16 ml (8.334 mmoles) of triethylamine cooled at 00, add dropwise 5951 µl (7.696 mmoles) (2.4 eq) of $CH_3SO_2Cl$ in 2 mL of dry

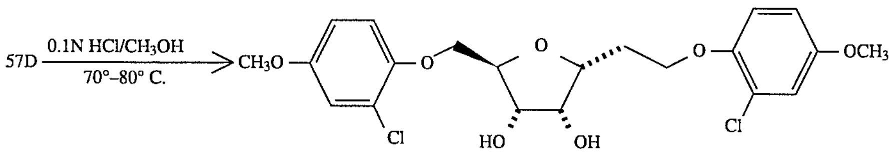

57E $CH_2C_{12}$. Stir the so-formed reaction mixture for 3 hours as the temperature slowly rises to 25° C. Add thereto 25 ml of $CH_2Cl_2$ and wash the organic layer with water and thereafter with brine. Dry the organic layer over $Na_2SO_4$ and remove solvent to form a residue. Add 10 ml of dry DMSO to the so-formed residue. To the so-formed solution add 2.3 g (0.01282 moles) of the sodium 2-chloro-4-methoxyphenoxide and stir the so-formed reaction mixture for 48 hrs. Add $CH_2Cl_2$, wash the organic layer with water and 10% NaOH in water, brine and dry over $Na_2SO_4$. Remove the solvent at reduced pressure to form a residue. Purify the residue on silica gel column chromatography eluting with 50% $CH_2Cl_2$ hexane to 100% $CH_2Cl_2$. The 200 MHz NMR spectrum of the recovered product is consistent with the proposed structure.

(e) Heat a mixture of 385 mg (0.7715 mmoles) of the product of step (d) in 40 ml of 0.1N HCl at 70°–80° for 1 ½ hr and continue to stir the so-formed reaction mixture overnight as the reaction cools to ambient. Starting material still coats the bottom of flask. Add 20 mL of $CH_3OH$. Heat the reaction mixture at 70°–80° for 3 ½ hours and a solution is formed. Cool to room temperature, remove the $CH_3OH$ and adjust pH to 12 with NaOH and saturate with NaCl. Extract the aqueous phase with 3 portions of ethyl acetate. Dry the combined extracts over $Na_2SO_4$, and remove solvent at reduced pressure to produce 345 mg of the diol. The $200MH_2$ NMR and mass spectra were consistent with the proposed structure.

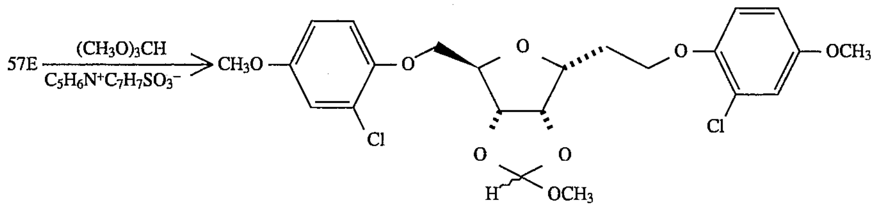

57F (f) To a solution of 21 5 mg (0.4684 mmole) of the product of Step (e)in 5 ml of dry $CH_2Cl_2$, add 307 µl (298 rag, 6 eq) $HC(OCH_3)_3$ and 58.8 mg (0.2342 mmole, 0.5 eq) of pyridinium p-toluene sulfonate and stir the so-formed reaction mixture overnight at ambient temperature (25° C.). Wash the reaction mixture with aq $NaHCO_3$, water, brine and dry the organic layer over $Na_2SO_4$. Purify the mixture by silica gel chromatography eluting with 10% ETOAc/Hexane to 40% ETOAc/Hexane to obtain 160 mg of the desired compound (68% yield). The 200 MHz NMR spectrum is consistent with the proposed structure.

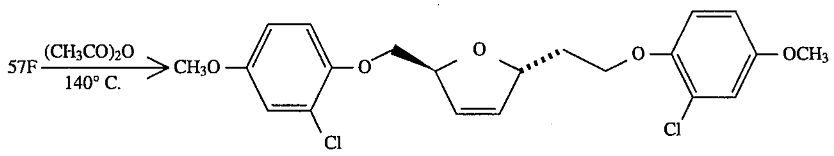

(g) Heat a solution of 156 mg of the product of step (f)in 10 ml of acetic anhydride at a temperature of 140° C. overnight. No starting material is found by TLC. Remove the solvent at reduced pressure. Add $CH_2Cl_2$ to the so-formed residue and stir the organic layer with $NaHCO_3$ for 2 hrs. Separate and dry the organic layer over $Na_2SO_4$. Remove solvent and purify the residue on a silica gel column eluting with 75% $CH_2Cl_2$/ hexane to provide 40 mg of the desired product. The 200 MHz NMR and mass spectra are consistent with the proposed structure.

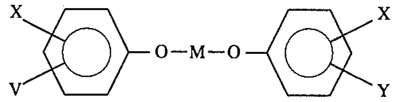

| Example | W | V | M | X | Y |
|---|---|---|---|---|---|
| 58 | 2-Cl | 4-$CH_3O$— | 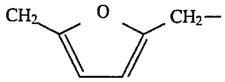 | 2-Cl | 6-Cl |
| 59 | " | " | " | 2-Cl | 5-Cl |
| 60 | " | " | " | 2-Cl | 4-Cl |
| 61 | " | " | " | 2-F | 6-F |
| 62 | " | " | " | 2-$CH_3$ | 4-$CH_3$ |
| 63 | " | " | 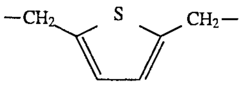 | 2-Cl | 6-Cl |
| 64 | " | " | " | 2-Cl | 5-Cl |
| 65 | " | " | " | 2-F | 4-F |
| 66 | " | " | " | 2-$CH_3$ | 5-$CH_3$ |
| 67 | " | " | 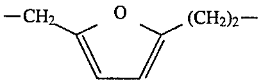 | 2-Cl | 6-Cl |
| 68 | " | " | | 2-Cl | 5-Cl |
| 69 | " | " | " | 2-F | 4-F |
| 70 | " | " | " | 2-Cl | 4-$CH_3O$ |
| 71 | 2-Cl | 5-Cl | " | 2-Cl | " |
| 72 | 2-Cl | 6-Cl | " | " | " |
| 73 | 2-F | 4-F | " | " | " |
| 74 | 2-Cl | 6-Cl | 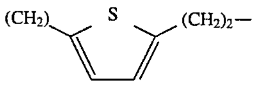 | " | " |
| 75 | 2-Cl | 5-Cl | " | " | " |
| 76 | 2-Cl | 4-Cl | " | " | " |
| 77 | 2-Cl | 4-$CH_3O$ | " | " | " |
| 78 | " | " | " | 2-Cl | 5-Cl |
| 79 | " | " | " | 2-F | 4-F |
| 80 | " | " | " | 2-F | 6-F |
| 81 | 2-Cl | 4-$CH_3O$ | 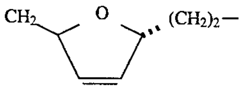 | 2-Cl | 6-Cl |
| 82 | " | " | " | 2-Cl | 5-Cl |
| 83 | " | " | " | 2-Cl | 5-Cl |
| 84 | " | " | " | 2-Cl | 4-$CH_3O$ |
| 85 | 2-Cl | 6-Cl | " | " | " |
| 86 | 2-Cl | 5-Cl | " | " | " |
| 87 | 2-F | 4-F | " | 2-Cl | 4-$CH_3O$ |
| 88 | 2-Cl | 6-Cl | 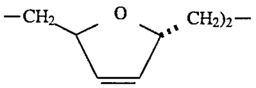 | " | " |
| 89 | 2-Cl | 5-Cl | " | " | " |
| 90 | 2-Cl | 5-Cl | " | " | " |
| 91 | 2-F | 6-F | " | " | " |
| 92 | 2-F | 5-F | " | " | " |
| 93 | 2-Cl | 4-$CH_3O$ | " | " | " |
| 94 | 2-Cl | 6-Cl | " | 2-Cl | 4-$CH_3O$ |
| 95 | 2-Cl | 5-Cl | " | " | " |
| 96 | 2-F | 4-F | " | " | " |
| 97 | 2-$CH_3$ | 6-$CH_3$ | " | " | " |
| 98 | 2-$CH_3$ | 5-$CH_3$ | " | " | " |
| 99 | 2-F | 5-F | " | " | " |
| 100 | 2-F | 6-F | " | " | " |

Follow the procedures of Scheme A, and Examples 15 and 27 except substitute equivalent quantities of HO—M—OH for the diols and phenols of Examples 15 and 57, respectively.

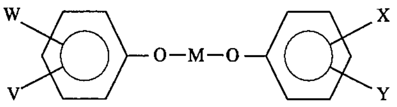

| | | | | | |
|---|---|---|---|---|---|
| 101 | 2-Cl | 4-$CH_3O$ | 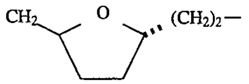 | 2-Cl | 6-Cl |
| 102 | " | " | " | 2-Cl | 5-Cl |
| 103 | " | " | " | 2-Cl | 5-Cl |
| 104 | " | " | " | 2-Cl | 4-$CH_3O$ |
| 105 | 2-Cl | 6-Cl | " | " | " |
| 106 | 2-Cl | 5-Cl | " | " | " |
| 107 | 2-F | 4-F | " | 2-Cl | 4-$CH_3O$ |
| 108 | 2-Cl | 6-Cl | 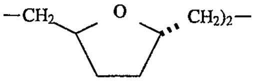 | " | " |
| 109 | 2-Cl | 5-Cl | " | " | " |
| 110 | 2-Cl | 5-Cl | " | " | " |
| 111 | 2-F | 6-F | " | " | " |
| 112 | 2-F | 5-F | " | " | " |
| 113 | 2-Cl | 4-$CH_3O$ | " | " | " |
| 114 | 2-Cl | 6-Cl | " | 2-Cl | 4-$CH_3O$ |
| 115 | 2-Cl | 5-Cl | " | " | " |
| 116 | 2-F | 4-F | " | " | " |
| 117 | 2-$CH_3$ | 6-$CH_3$ | " | " | " |
| 118 | 2-$CH_3$ | 5-$CH_3$ | " | " | " |
| 119 | 2-F | 5-F | " | " | " |
| 120 | 2-F | 6-F | " | " | " |

Follow the procedure of Examples 81 to 100 except substitute equivalent quantities of HO—M—OH which have been hydrogenated with $H_2$/ Pd to produce the saturated tetrahydrofurans for the dihydropyran-diols of Example 81 to 100, respectively.

In a like manner, the 2,5 furan-diols used as starting materials in Example 58–62 and 67 to 73 may be hydrogenated to produce the isomeric 2,5-tetrahydrofuran-diols which may be separated into pure compounds and then used to produce additional compounds within the scope of this invention.

Example 121

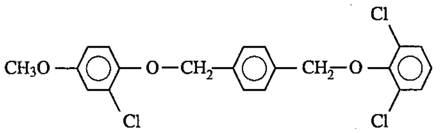

a) Preparation of Methyl 4-chloromethylbenzoate

To a solution of 100 g (0.60175 moles) of methyl 4-hydroxymethylbenzoate in 600 mL of dry $CH_2Cl_2$. add 109 mL (79.1 g) of TEA and cool the so-formed reaction mixture to 0° C. Add, dropwise over a 2 hour period, 55.8 mL (0.722 mole, 1.2 eq) of methanesulfonyl chloride in 150 mL of dry $CH_2Cl_2$. Allow the so-formed stirred reaction mixture to warm slowly to room temperature over a 48 hr period. TLC shows no starting material remains. Add water, separate the layers and wash the organic layer successively with water, saturated $NaHCO_3$ and brine. Dry the organic layer over $Na_2SO_4$. Remove the organic solvent under reduced pressure to produce 98.45 g of (88.6 % of theory) of the title compound as a crystalline solid.

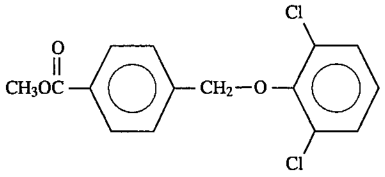

(b) Preparation of

Stir a mixture of 100 g (0.61324 moles) of 2,6-dichlorophenol, 24.5 g (0.6134 moles) of NaOH and 50 mL of anhydrous ethanol at 25° for 1 hour. Remove the ethanol at reduced pressure to produce 114 g of an off-white solid of sodium 2,6-dichlorophenoxide.

Stir a mixture of 100 g of the product prepared as described in step (a)in 500 mL of dry DMF and 81.1 g (0.54168 moles) of Nal and 150 g (0.8108 moles, 1.5 eg) of sodium 2,6-dichlorophenoxide at room temperature overnight. Add water to the so-formed formed reaction mixture to produce a precipitated solid. Add $CH_2Cl_2$ to dissolve the precipitated solid. Wash the $CH_2Cl_2$ layers successively with four volumes of a 5% aqueous NaOH solution, water and brine. Separate and dry the organic layer over $Na_2SO_4$. Remove the solvent under reduced pressure to produce 164.5 g (97.6% of theory) of the title compound. The 200 $MH_z$ NMR spectrum is consistent with the proposed ester structure

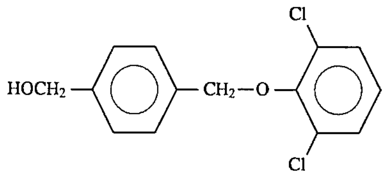

(c) Preparation of

To a cooled solution of 5 g (0.016 moles) of the ester of step (b) in 30 mL of freshly distilled THF, add 0.96 (0.0253 moles) of $LiAlH_4$ portionwise, with stirring. Follow disappearance of the starting material by TLC. Cool the reaction mixture and add thereto, dropwise, 1 mL of water, 1 mL of 15% aqueous NaOH and 3 mL of $H_2O$ to produce a granular precipitate. Add 2 g of anhydrous $Na_2SO_4$ and stir the so-formed mixture for 25 minutes. Remove the precipitate by filtration and remove the THF at reduced pressure to provide 3.9 g (86.6% of theory) of the title compound. The 200 MHz NMR spectrum is consistent with the proposed alcohol structure.

(d) Preparation of 2-chloro-4-methoxyphenol.

To a solution of 250 g of 4-methoxyphenol in 600 mL of $CHCl_3$, add dropwise, over a 3 hour period 190 mL of $SO_2Cl_2$ in 200 mL of $CHCl_3$. Stir the so-formed reaction mixture at 25° C. for 18 hours. The reaction mixture contained no starting material by TLC. Remove the solvent and $SO_2Cl_2$ at reduced pressure and distill the so-formed product at reduced pressure to produce 21 0 g of the title compound. The $200MH_2$ NMR was consistent with the proposed structure.

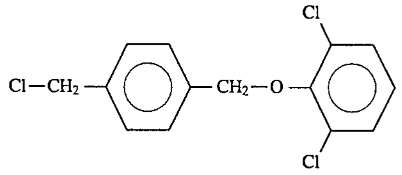

(e) Preparation of

To a solution at 0° C. of 131 g (0.4626 moles) of the product of step (c)in 800 mL of dry $CH_2Cl_2$ and 83.8 mL (0.60138 moles) of TEA, add dropwise over a 1 hour period 42.96 mL (0.555 moles, 1.2 eq) of methane sulfonylchloride in 150 mL of dry $CH_2Cl_2$. Allow the stirred solution to warm slowly to 25° C. over a 48 hr period. Add water and wash the separated organic layer with water, 10% aqueous NaOH, brine and dry the organic layer over $Na_2SO_4$. Remove the solvent at reduced pressure to provide 127.5 g (91.4% of theory) of the title compound. The 200 $MH_z$ NMR spectrum is consistent with the proposed structure.

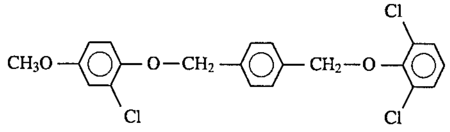

(f) Preparation of

Stir a mixture of 95.66 g (0.31 71 moles) of the product of step (e), 400 mL of dry DMF, 60.33 g (0.3805, 1.2eq) of 2-chloro-4-methoxyphenol of step (d) and 15.85 (0.3963 moles, 1.25 eq) of crushed NaOH pellets at ambient temperature overnight. No starting material is detected by TLC in the so-formed reaction mixture. Add ETOAc and wash the so-formed layer successively with 5 volumes of water, brine and dry the separated organic layer over $Na_2SO_4$. Remove the solvents at reduced pressure to provide 130 g of crude product. Purify the crude product by recrystallization from anhydrous ethanol to provide 112 g of the title product. The 200 $MH_z$ NMR and mass spectra are consistent with the structure of the proposed product.

What is claimed is:

1. A compound represented by formula I $Ar_1—O—M—O—Ar_2$ I wherein $Ar_1$ and $Ar_2$ are independently substituted phenyl or substituted pyridinyl, the substituents on said phenyl or pyridinyl being independently selected from one, two or three of halogen ($C_1$–$C_{10}$) alkyl ($C_1$–$C_{10}$) perhaloalkyl, ($C_1$–$C_{10}$) alkoxy, halogen, carbamyl, dialkylcarbamyl ($C_1$–$C_{10}$) alkoxycarbonyl, oxazolinyl, and ($C_1$–$C_{10}$) alkyl substituted by ($C_1$–$C_{10}$) alkoxy, hydroxy, or ($C_1$–$C_{10}$) alkoxycarbonyl;

M is

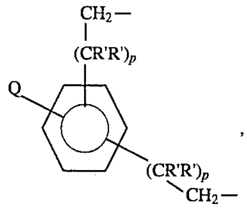 ,

M-1

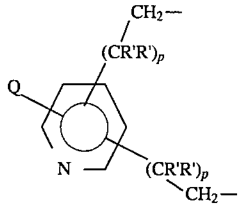

M-2

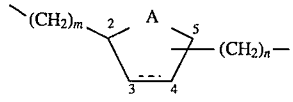

M-3

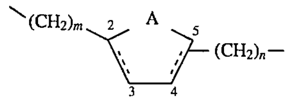

M-4

O is oxygen

R' is ($C_1$–$C_3$) alkyl or H;

A is oxygen or sulfur;

Q is selected from hydrogen, halogen, nitro, ($C_1$–$C_6$) alkyl, ($C_1$–$C_6$) perhaloalkyl, ($C_1$–$C_6$) alkylthio, and ($C_1$–$C_6$) alkylsulfonyl;

the dotted lines in M-3 and M-4 between the carbons 2 and 3, 3 and 4 and 4, and 5 mean that the bonds between carbons 2 and 3, and 3 and 4, and 4 and 5 may each be a single or double bond;

n=1 or 2;

m=1 or 2;

p=0 or 1; and or pharmaceutically acceptable salts thereof; with the proviso that when Q is hydrogen, p is not 0.

2. A compound of claim 1 wherein M is M-1, i.e.,

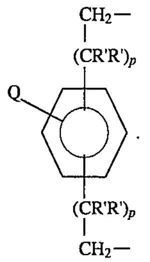

M-1

3. A compound of claim 1 wherein M is M-2, i.e.,

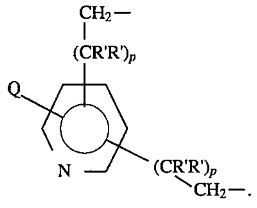

M-2

4. A compound of claim 1 wherein M is

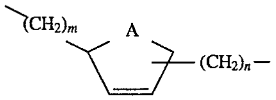

5. A compound of claim 1 wherein M is

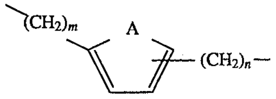

6. A compound of claim 1 wherein $Ar_1=Ar_2$.

7. A compound of claim 1 wherein the substituents on $Ar_1$ and $Ar_2$ are independently 2,4,2,5 or 2,6-di-halo and 4-($C_1$–$C_6$)alkoxy.

8. A compound of claim wherein $Ar_1$ and $Ar_2$ are each 4-($C_1$–$C_6$)alkoxy)-2-halophenyl.

9. A pharmaceutical composition for treating viral infections which comprises an antivirally effective amount of a compound of claim 1 and a pharmaceutically carrier.

10. A pharmaceutical composition of claim 1 adapted for oral administration.

11. A method for treating or preventing a picomaviral infection in a mammal in need of such treating or preventing which comprises administering to such a mammal an anti-picomaviral effective amount of a compound of claim 1.

12. A compound of claim 1 wherein $Ar_1$ and $Ar_2$ are each independently 4-($C_1$–$C_{10}$)alkoxyl)-2-halo, 2-($C_1$–$C_{10}$)alkoxyl-4-halo; 2-($C_1$–$C_{10}$)alkoxyl-6-halo; 2,4-dihalo, 2,6-dihalo, 2,5-dihalo, 2,4 di-($C_1$–$C_{10}$)alkyl; 2,5-di-($C_1$–$C_{10}$)alkyl or 2.6-di-($C_1$–$C_{10}$)alkyl.

13. A compound of claim 1 wherein $Ar_1$ and $Ar_2$ are independently

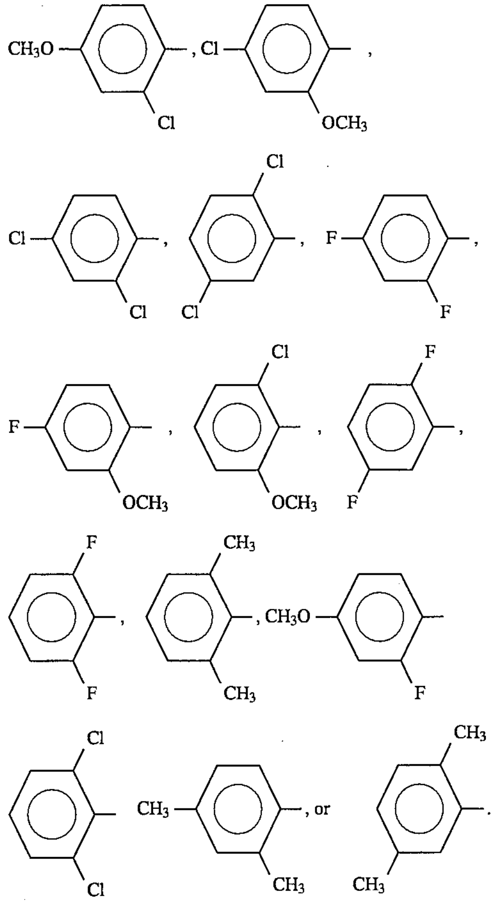

* * * * *